(12) United States Patent
Travis et al.

(10) Patent No.: US 6,864,363 B2
(45) Date of Patent: Mar. 8, 2005

(54) DIPEPTIDYLPEPTIDASES AND METHODS OF USE

(75) Inventors: James Travis, Athens, GA (US); Jan S. Potempa, Athens, GA (US); Agnieszka Banbula, Chapel Hill, NC (US); Marcin Bugno, Chapel Hill, NC (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 10/008,355

(22) Filed: Nov. 8, 2001

(65) Prior Publication Data

US 2002/0164759 A1 Nov. 7, 2002

Related U.S. Application Data

(60) Provisional application No. 60/246,827, filed on Nov. 8, 2000.

(51) Int. Cl.⁷ .......................... C07H 21/04; C12N 9/48
(52) U.S. Cl. ..................................... 536/23.2; 435/212
(58) Field of Search ..................................... 536/223.2

(56) References Cited

U.S. PATENT DOCUMENTS

| | | | | |
|---|---|---|---|---|
| 5,223,404 A | 6/1993 | Suido et al. | ................... | 435/24 |
| 5,432,055 A | 7/1995 | Evans et al. | ................... | 435/6 |
| 5,475,097 A | 12/1995 | Travis et al. | ................ | 536/23.2 |
| 5,521,081 A | 5/1996 | Inaoka et al. | ................ | 435/212 |
| 5,523,390 A | 6/1996 | Travis et al. | ................ | 536/23.2 |
| 5,824,791 A | 10/1998 | Progulske-Fox et al. | .... | 536/237 |
| 5,919,690 A | 7/1999 | Knap et al. | ................... | 435/208 |
| 5,981,164 A | 11/1999 | Wikström | ....................... | 435/4 |
| 6,129,917 A | 10/2000 | Potempa et al. | ......... | 424/184.1 |
| 6,274,718 B1 | 8/2001 | Travis et al. | ................ | 536/23.2 |
| 6,284,511 B1 | 9/2001 | Inaoka et al. | ............... | 435/212 |
| 6,444,799 B1 * | 9/2002 | Ross | ........................ | 536/23.1 |

FOREIGN PATENT DOCUMENTS

| | | | | |
|---|---|---|---|---|
| EP | 0 255 341 | 3/1988 | ............ | C12Q/1/36 |
| JP | 2-5580 | 10/1990 | ........... | C12N/15/57 |
| WO | WO 94/23022 | 10/1994 | ............ | C12N/9/40 |
| WO | WO 97/44447 | 11/1997 | ........... | C12N/15/10 |
| WO | WO 00/52147 | 9/2000 | ........... | C12N/15/57 |

OTHER PUBLICATIONS

Wisehart et al A single mutation converts a novel phosphotyrosine binding domain into a dual–specificity phosphatase. J Biol Chem. Nov. 1995 10;270(45):26782–5.*

Witkowski et al Conversion of a beta–ketoacyl synthase to a malonyl decarboxylase by replacement of the active–site cysteine with glutamine. Biochemistry. Sep. 1999 7;38(36):11643–50.*

Duncan et al *Porphyromonas gingivalis* Genome Project http://www.pginigvalis.org/ Feb. 2, 2002 Strain Info, Introduction, Library construction, and Sequencing.*

Ross et al, *P. gingivalis* nucleotides and uses thereof. from US Pat#6444799 SEQ ID No.: 726. 2002 (filing date Dec. 23, 1998) Alignment with SEQ ID No.: 1 and SEQ ID No.: 2.*

Ross et al, *P. gingivalis* nucleotides and uses thereof. from US Pat#6444799 SEQ ID No.: 726. 2002 (filing date Dec. 23, 1998) EMBOSS–Transeq Reading Frames 1–3.*

Ross et al, *P. gingivalis* nucleotides and uses thereof. from US Pat#6444799 SEQ ID No.: 726. 2002 (filing date Dec. 23, 1998) Blast search.*

Simpson et al The genome sequence of the plant pathogen *Xylella fastidiosa*. The Xylella fastidiosa Consortium of the Organization for Nucleotide Sequencing and Analysis. Nature. Jul. 13, 2000;406(6792):151–7. EMBL Acc#AE004008 alignment with SEQ ID No.: 2.*

TIGR The Institute for Genomic Research. Frequently Asked Questions. Question 10: How can I download your data? URL; http://www.tigr.org/about/faq.shtml. Oct. 10, 2002.*

Altschul et al., "Gapped Blast and PSO–Blast: a new generation of protein database search probrams," *Nucl. Acids Res.*, 1997; 25(17):3389–3402.

Ausubel ed. *Current Protocols in Molecular Biology*, John Wiley & Sons, Inc., 1994, Cover page, Title page, and Table of Contents only. (12 pgs.).

Awano et al., "Sequencing, expression and biochemical characterization of the *Porphyromonas gingivalis* pepO gene encoding a protein homologous to human endothelin––converting enzyme," *FEBS Letters*, 1999; 460:139–44.

Banbula et al., "Emerging Family of Proline–Specific Peptidases of *Porphyromonas gingivalis:* Purification and Characterization of Serine Dipeptidyl Peptidase, a Structural and Functional Homologue of Mammalian Prolyl Dipeptidyl Peptidase IV," *Infect. Immun.*, Mar. 2000; 68(3):1176–82.

Banbula et al., "Prolyl Tripeptidyl Peptidase from *Porphyromonas gingivalis*," *J. Biol. Chem.*, Apr. 2, 1999; 274(14):9246–52.

Banbula et al., "*Porphyromonas gingivalis* DPP–7 Represents a Novel Type of Dipeptidylpeptidase" *The Journal of Biological Chemistry*, Mar. 2, 2001; 276(9):6299–6305.

(List continued on next page.)

*Primary Examiner*—Rebecca E. Prouty
*Assistant Examiner*—Sheridan L. Swope
(74) *Attorney, Agent, or Firm*—Mueting, Raasch & Gebhardt, P.A.

(57) ABSTRACT

The present invention provides isolated polypeptides, dipeptidylpeptidases, active analogs, active fragments, or active modifications thereof, having amidolytic activity for cleavage of a peptide bond between the second and third amino acids from the N-terminal end of a target polypeptide, wherein the target polypeptide has an aliphatic or an aromatic residue as a substituent on the α-carbon atom of the second amino acid from the N-terminal end of the peptide. Isolated nucleic acids encoding dipeptidylpeptidases are also provided, as are methods of reducing growth of a bacterium by inhibiting a dipeptidylpeptidase.

3 Claims, 10 Drawing Sheets

OTHER PUBLICATIONS

Barrett et al., *Handbook of Proteolytic Enzymes*, 1998, Academic Press, London, Cover page, Publication page, and Table of Contents only. (13 pgs).

Beauvais et al., "Biochemical and Antigenic Characterization of a New Dipeptidyl–Peptidase Isolated from *Aspergillus fumigatus*," *J. Biol. Chem.*, 1997 Mar. 7; 272(10):6238–44.

Berger et al., "Mapping the active site of papain with the aid of peptide substrates and inhibitors," *Phil. Trans. Roy. Soc. Lond. B.*, 1970; 257:249–64.

Birkedal–Hansen et al., "Characterization of collegenolytic activity from strains of *Bacteroides gingivalis*," *J. Periodontal Res.*, Jul. 1988; 23(4):258–264.

Bourgeau et al., "Cloning, Expression, and Sequencing of a Protease Gene (tpr) from *Porphyromonas gingivalis* W83 in *Escherichia coli*," *Infect. Immun.*, 1992 Aug., 60(8):3186–92.

Brosius et al., "Gene Organization and Primary Structure of a Ribosomal RNA Operon from *Escherichia coli*," *J. Mol. Biol. Biol.*, 1981; 148(16):107–127.

Carmona et al., "Nucleotide sequence of the serine protease gene of *Staphylococcus aureus*, strain V8," *Nucleic Acids Res.*, 1987; 15:6757.

Chen et al., "Purification and Characterization of a 50–kDa Cysteine Proteinase (Gingipain) from *Porphyromonas gingivalis*," *J. Biol. Chem.*, Sep. 15, 1992; 267(26):18896–901.

Church et al., "Genomic sequencing," *Proc. Natl. Acad. Sci USA*, Apr. 1984; 81:1991–1995.

Curtis et al., "Molecular genetics and nonmenclature of proteaes of *Porphyromonas gingivalis*," *J. Periodontal Res.*, 1999; 34:464–72.

Ellis et al., "Dipeptidyl Arylamidase III of the Pituitary," *J. Biol. Chem.*, 1967 Oct. 25; 242(20):4623–29.

Kato et al., "Sequence Analysis and Characterization of the *Porphyromonas gingivalis* prtC Gene, Which Expresses a Novel Collagenase Activity," *J. Bacteriol.*, Jun. 1992; 174(12):3889–95.

Kiyama et al., "Sequence analysis of the *Porphyromonas gingivalis* dipeptidyl peptidase IV gene," *Biochim. Biophys. Acta.*, 1998; 1396:39–46.

Kornman, "Controlled–Release Local Delivery Antimicrobials in Periodontics: Prospects for the Future," *J. Periodontol.*, Aug. 1993; 64(8):782–91.

Kumagai et al., "Enzymatic Properties of Dipeptidyl Aminopeptidase IV Produced by the Periodontal Pathogen *Porphyromonas gingivalis* and Its Participation in Virulence," *Infect. Immun.*, Feb. 2000; 68(2):716–24.

Lawson et al., "Biochemical Characterization of *Porphyromonas (Bacteriodes) gingivalis* Collagenase," *Infect. Immun.*, Apr. 1992; 60(4):1524–29.

Matsudaria et al., "Sequence from Picomole Quantities of Proteins Electroblotted onto Polyvinylidene Difluoride Membranes," *J. Biol. Chem.*, Jul. 25, 1987; 262(21):10035–38.

McGuire et al., "Purification and Characterization of Dipeptidyl Peptidase I from Human Spleen," *Arch. Biochem. Biophys.*, Jun. 1992; 295(2):280–88.

Microbial Genomes Blast Databases [online]. National Center for Biotechnology Information, 2001 [retrieved on Jul. 2, 2002]. Retrieved from the Internet: <URL:http://www.ncbi.nlm.nih.gov/Microb_blast/unfinishedgenome-.html>. (4 pgs.).

Nelson et al., "Purification and Characterization of a Novel Cysteine Proteinase (Periodontain) from *Porphyromonas gingivalis*," *J. Biol. Chem.*, Apr. 30, 1999; 274(18):12245–51.

Ogasawara et al., "Two types of Novel Dipeptidyl Aminopeptidases from Pseudomonas sp. Strain WO24," *J. Bacteriol.*, Nov. 1996; 178(21):6288–95.

Otogoto et al., "Isolation and Characerization of the *porphyromonas gingivalis* prtT Gene, Coding for Protease Activity," *Infect. Immun.*, Jan. 1993; 61(1):117–23.

Pohl et al., "Assignment of the three disulfide bonds in ShK toxin: A potent potassium channel inhibitor from the sea anemone *Stichodactyla helianthus*," *Lett. Pepetide Sci.*, 1994; 1:291–97.

Rosenfeld et al., "In–Gel Digestion of Proteins for Internal Sequence Analysis after One– or Two–Dimensional Gel Electrophoresis," *Anal. Biochem.*, 1992; 203:173–79.

Sambrook et al., *Molecular Cloning: A Laboratory Manual*, Cold Spring Harbor Laboratory Press, 1989, Cover Page, Publication Page, and Table of Contents only. (30 pgs.).

Schägger et al., "Tricine–Sodium Dodecyl Sulfate–Polyarylamide Gel Electrophoresis for the Separation of Proteins in the Range from 1 to 100 kDa," *Anal. Biochem.*, 1987; 166:368–79.

TIGR: The Institute for Genomic Research, [online], [retrieved on Jul. 2, 2002] Retrieved from the Internet: <URL:http://www.tigr.org/>. (1 pg.).

Travis et al., "The Role of Bacterial and Host Proteinases in Periodontal Disease," *J. Adv. Exp. Med. Biol.*, 2000; 477:455–65.

Travis, James. "Bacterial Proteinases in Periodontal," Grant Abstract, Grant No. 5R01DE09761–09 [online]. National Institute of Dental Research, Aug. 1, 1991–Dec. 31, 2001 [retrieved on Nov. 8, 2000]. Retrieved from the Internet: <URL:http://commons.cit.nig.gov/crisp_lib.getdoc?textkey=6137915&p_query=&ticket+18301...>; 2 pgs.

Travis, James "Bacterial Proteinases in Periodontal Disease," Grant Abstract, Grant No. 5R01DE009761–10 [online]. National Institute of Dental & Craniofacial Research, Aug. 1, 1991–Dec. 31, 2001 [retrieved on Oct. 9, 2001]. <URL:http://commons.cit.nig.gov/crisp_lib.getdoc?textkey=6342385&p...>; 2 pgs.

Vacheron et al., "Caractérisation d'une nouvelle endopeptidase spécifiques des liaisons γ–D–glutamyl–L–lysine et γ–D–glutamyl–L)meso–diaminopimélate de substrats peptidoglycaniques, chez *Bacillus spaericus* 9602 au cours de la sporulation," *Eur. J. Biochem.*, 1979; 100:189–96.

Abbott et al., "Genomic organization, exact localization, and tissue expression of the human CD26 (dipeptidyl peptidase IV) gene," *Immunogentics, 40:*331–338 (1994).

Abiko et al., "Glycylprolyl Dipeptidylaminopeptidase from *Bacterioides gingivalis*," *J. Dent. Res., 64*(2):106–111 (1985).

Anderson et al., "Presence and possible role of a renal brush–border Gly–Pro–X–releasing exopeptidase," *Amer. Phys. Soc.*, F649–F655 (1987).

Banbula et al., "Unusual Processing of Proteins and Polypeptides During the Groth of *Porphyromonas gingivalis*: Implications of a Primary Role for Prolyl Di– and Tripeptidyl–Peptidases," *J. Dent. Res., 78:*466, Abstract No. 2888 (May, 1999).

Banbula et al., "Unusual Procesing of Proteins and Polypeptides During the Growth of *Porphyromonas gingivalis*: Implication of a Primary Role for Prolyl Di and Tripeptidyl–Peptidases," poster presentation (6 pages) at Edward H. Hatton Awards Comeptition, Vancouver (B.C.), Canada (Mar. 9, 1999).

Barua et al., "Purification of an 80,000–$M_r$Glycylprolyl Peptidase from *Bacterioides gingivalis*, " *Infect. Immun.*, 57(8):2522–2528 (1989).

Binnie et al., "Isolationg and Characterization of Two Genes Encoding Proteases Associated with the Mycelium of *Streptomyces lividans* 66," *J. Bact.*, 177(21):6033–6040 (1995).

Dashper et al., "Amino Acid and Peptide Uptake by *Porphyromonas gingivalis*," *J. Dent. Res.*, 77(5):1133, Abstract No. 36 (1998).

Fülöp et al., "Prolyl Oligopeptidase: An Unusual Beta–Propeller Domain Regulates Proteolysis," *Cell*, 94(2):161–170 (1998).

Greinier et al., "Isolation of a Membrane–Associated *Bacteroides gingivalis* Glycylprolyl Protease," *Infect. Immun.*, 55(12):3131–3136 (1987).

Hillier et al., GenBank Accession No. R11686, <http://www.ncbi.nlm.nih.gov/entrez/query.fcgi?cmd=Retrieve&db=nucleotide&list_uids=7...>, created Sep. 2002 (2 pgs.).

Hinode et al., "Purification and Characterization the Three Types of Proteases from Culture Supernatants of *Porphyromonas gingivalis*," *Infect. Immun.*, 59(9):3060–3068 (1991).

Kabashima et al., "Cloning, Sequencing, and Expression of the Dipeptidyl Peptidase IV Gene form *Flavobacterium meningosepticum* in *Escherichia coli*," *Arch. Biochem. Biophys.*, 320(1):123–128 (1995).

Kuramitsu, "Proteases of *Porphyromonas gingivalis:* what don't they do?, " *Oral Micro. Immun.*, 13:263–270 (1998).

Martinsson et al., "Localization of the Human Tripeptidyl Peptidase II Gene (TPP2) to 13q32–q33 by Nonradioactive in Situ Hybridization and Somatic Cell Hybrids," *Genomics*, 17:493–495 (1993).

Nakamura et al., "Cloning of the Gene Encoding a Glycylprolyl Aminopeptidase from *Porphyromonas gingivalis*," *Arch. Oral Biol.*, 37(10):807–812 (1992).

Potempa et al., "Host and *Porphyromonas gingivalis* Proteinases in Periodontitis: A Biochemical Model of Infection and Tissue Destruction," *Perspect. Drug Discovery Design*, 2;445–458 (1995).

Rawlings et al., "A New Family of Serine–type Peptidases Related to Prolyl Oligopeptidase," *Biochem. J.*, 279(Pt. 3):907–908 (1991).

Renn et al., "Characterization and Cloning of Tripeptidyl Peptidase II from the Fruit Fly, *Drosophila metlanogaster,*" *J. Biol. Chem.*, 273(90):19178–19182 (1998).

Slots et al., "The Occurence of *Actinobacillus actinomycetemcomitans, Bacteroides gingivalis* and *Bacterioides intermedius* in Destructive Peridontal Disease in Adults," *J. Clin. Periodontol.*, 13:570–577 (1986).

Stenfors et al., "Characterization of Endogenous Neuropeptide Y in Rat Hippocampus and its Metabolism by Nanospray Mass Spectrometry," *J. Biol. Chem.*, 272(9):5747–5751 (1997).

Walter et al., "Proline Specific Endo– and Exopeptidases," *Mol. Cell. Biochem.*, 30(2):111–127 (1980).

Simpson et al., "The genome sequence of the plant pathogen *Xylella fastidiosa*," *Nature*, Jul. 13, 2000;406:151–157.

XP002219380, "Zylella fastidiosa 9a5c", created on Jul. 18, 2000 [retrieved from EMBL Database] Accession No. AE004008 (3 pgs.).

XP002219381, "Glutamyl endopeptidase precursor (EC3.4.21.19)", created on Mar. 20, 1987; [retrieved from EMBL Database] Accession No. P04188 (1 pg.).

National Center for Biotechnology Information, National Library of Medicine, National Institutes of Health, GenBank Locus CAC06168, Accession No.CAC06168, "Glutamyl endopeptidase [Staphylococcus warneri]," [online]. Bethesda, MD [retrieved on Oct. 23, 2003]. Retrieved from the Internet:<URL:http: //www.ncbi/nlm.nih.gov/entrez/query.fcgi?cmd=Retrieve&db=protein&list_uids=9968803&dopt=GenPept&term=9968803&qty=1>; 1 pg.

Yokoi et al., Genetic and biochemical characterization of glutamyl endopeptidase of Staphylococcus warneri M, *Gene*, vol. 281, Title page and pp. 115–122 (2001).

\* cited by examiner

Fig. 4a

SEQ ID NO:1  atgcaaatgaaattaaaaagtattcttctcgagcagccctgctgttgggtgcttcagggtagccaaagccgacaaaggcatgtggctc  90
SEQ ID NO:2   M  Q  M  K  L  K  S  I  L  L  G  A  A  L  L  L  G  A  S  G  V  A  K  A  D  K  G  M  W  L   30 ctcaacgaactcaatcaggagaatctgatgcgtgagctcggcttacgctccgttgattcgctctacagtttcgacaagccg  180
 L  N  E  L  N  Q  E  N  L  D  R  M  R  E  L  G  F  T  L  P  L  D  S  L  Y  S  F  D  K  P   60 tccattgccaatgccgtgttatcttcgtggcggatgtaccggtgatgtccgatcaggcctgatcttaccaaccaccactgc  270
 S  I  A  N  A  V  V  I  F  G  G  C  T  G  I  T  V  S  D  D  Q  G  L  I  F  T  N  H  H  C   90 ggatacggtgctatccagagccaaagcacggttgatcacgactatctgcgcagatgttcgtttctgcacgatggtgaggacttccg  360
 G  Y  G  A  I  Q  S  Q  S  T  V  D  H  D  Y  L  R  D  G  F  V  S  R  T  M  G  E  E  L  P   120 attccggtctttcgtgaagtatctgcgcaagatcgtgaagaagtaacggacaagtagaaggacagctcaagggtatcactgacgagatg  450
 I  P  G  L  S  V  K  Y  L  R  K  I  V  K  V  T  D  K  V  E  G  Q  L  K  G  I  T  D  E  M   150 gagcgtctgcgcaaagctcaggaggtatgccaagaactggccaagaactgctgcatctgtagagcctttc  540
 E  R  L  R  K  A  Q  E  V  C  Q  E  L  A  K  K  E  N  A  D  E  N  Q  L  C  I  V  E  P  F   180 tattccaacaacgaatacttcctctacgatgtattcaaggacgttcgtatgtattgctcctcccagctctgtaggtaagttc  630
 Y  S  N  N  E  Y  F  L  I  V  Y  D  V  F  K  D  V  R  M  V  F  A  P  P  S  S  V  G  K  F   210 ggaggcgatacggacaactggatgtggccgcgcacttcagcgactcacacggcgtatgccgtgccgacaaccggccggcc  720
 G  G  D  T  D  N  W  M  W  P  R  H  T  G  D  F  S  V  F  R  V  Y  A  G  A  D  N  R  P  A   240 gaatacagcaaggacaataaacctataagccgtttacttcgtgcctatccatgcaaggctacaaggctgacgactatgccatgacc  810
 E  Y  S  K  D  N  K  P  Y  K  P  V  Y  F  A  A  V  S  M  Q  G  Y  K  A  D  D  Y  A  M  T   270 atcggtttccgggcagtgcgatcgatcctggaagatcgtatcgaaaacgagaacaatcctcgtatcgaagtt  900
 I  G  F  P  G  S  T  D  R  Y  L  T  S  W  G  V  E  D  R  I  E  N  E  N  N  P  R  I  E  V   300 cgcggtatcaaggacatctgaaggaagcatgagcgcagatcaggctagagatcaaatatgccagcaagtatgctcagagtgct  990
 R  G  I  K  Q  G  I  W  K  E  A  M  S  A  D  Q  A  T  R  I  K  Y  A  S  K  Y  A  Q  S  A   330 aactattggaagaattcgatcggtatgaaccgcgtcttctgacgtgatataggtcgtgataggtcgtgaagctgccgaggaaagagcattcgca  1080
 N  Y  W  K  N  S  I  G  M  N  R  G  L  A  R  L  D  V  I  G  R  K  R  A  E  E  R  A  F  A   360

Fig. 4b

```
gactggatccgtaagaacggcaagagtgctgtctatggcgatgtattgtctctctgaaaaggcttataaggaggagcaaggccaac    1170
 D  W  I  R  K  N  G  K  S  A  V  Y  G  D  V  L  S  S  L  E  K  A  Y  K  E  G  A  K  A  N    390 cgtgagatgacttattgagcgagacgctcggtggtaccgagtggtgttcgttgcacagttttgcaacagtttgcacagttgctacaatcct    1260
 R  E  M  T  Y  L  S  E  T  L  F  G  G  T  E  V  V  R  F  A  Q  F  A  N  A  L  A  T  N  P    420 gatgctcatgccggtatcctcaaatcgcttgacgacaagtaccaagactactcccctcgctgaccgtaaggtgctgccgccatgctc    1350
 D  A  H  A  G  I  L  K  S  L  D  D  K  Y  K  D  Y  L  P  S  L  D  R  K  V  L  P  A  M  L    450 gatattgtacgccggcgtatccctgccgacaagagtgtggttccttatcgacaagatgtaatcgacaagaaattcaaaggcgacgaagaag    1440
 D  I  V  R  R  R  I  P  A  D  K  L  P  D  I  F  K  N  V  I  D  K  K  F  K  G  D  T  K  K    480 tatgcagacttcgtattcgacaagagtgtggttccttatagcgacaagttccatgctcaagtcatcaggcgtattcaggcgatgcgcaatgcc    1530
 Y  A  D  F  V  F  D  K  S  V  V  P  Y  S  D  K  F  H  A  M  L  K  S  M  D  K  E  K  F  A    510 aaggctatcgagaaagatccggcagtagagcgtcttttctttgctgcgtgagatgtaccccgacgtgctctgccgagcgatgccaacttcacc    1620
 K  A  I  E  K  D  P  A  V  E  L  S  K  S  V  I  A  A  R  A  I  Q  A  D  A  M  A  N  A    540 tatgccattgagaagggcaagcgtctctttttcttttgcgtttgctgagatgtaccccgacgtgctctgccgagcgatgccaacttcacc    1710
 Y  A  I  E  K  G  K  R  L  F  F  A  G  L  R  E  M  Y  P  P  G  R  A  L  P  S  D  A  N  F  T    570 atgcgtatgagctacggctccatcaaggatgagtttgccgtacagcgaccgcaggatatgaaccgcaggacgttgctggtacaactatcatacgacaggcaagggcgtattggag    1800
 M  R  M  S  Y  G  S  I  K  G  Y  E  P  Q  D  D  G  A  W  Y  N  Y  H  T  T  G  K  G  V  L  E    600 aagcaggatcctaagagcgatgagtttgccgtacagcgagaatatcctcgacctcttccgacctcttccgacaccaaaaactatgtgctatgccgagaac    1890
 K  Q  D  P  K  S  D  E  F  A  V  Q  E  N  I  L  D  L  F  R  T  K  N  Y  G  R  Y  A  E  N    630 ggtcagctccatatcgcttcctatcgaacaacgacatcacggcgtaactccggttagcccgtattcgataagaacggccgtcgatc    1980
 G  Q  L  H  I  A  F  L  S  N  N  D  I  T  G  G  N  S  G  S  P  V  F  D  K  N  G  R  L  I    660 ggtcttgcttgatggcaactggaagctatgagtgtgacatgagttgacaatcagcgtgacatccgc    2070
 G  L  A  F  D  G  N  W  E  A  M  S  G  D  I  E  F  E  P  D  L  Q  R  T  I  S  V  D  I  R    690 tacgttccttcatgattgacaaatgggtgcccggcagtgtccccgcagctcatccaagagctgaagttgatctaa    2139
 Y  V  L  F  M  I  D  K  W  G  Q  C  P  P  R  L  I  Q  E  L  K  L  I  *                       713
```

```
SEQ ID No:3   DPP-7 644 TGGNSGSPVFDKNGRLIGLAFDGNWEAMSGDIEFEPDLQRTISVDIRYVLFM 695
                       TGGNSGSPVF++    +IG+ + G     +G +   +++    +I  +  F
SEQ ID No:4   V-8   704 TGGNSGSPVFNEKNEVIGIHWGGVPNEFNGAVFINENVRNFLKQNIEDIHFA 863
```

Fig. 5

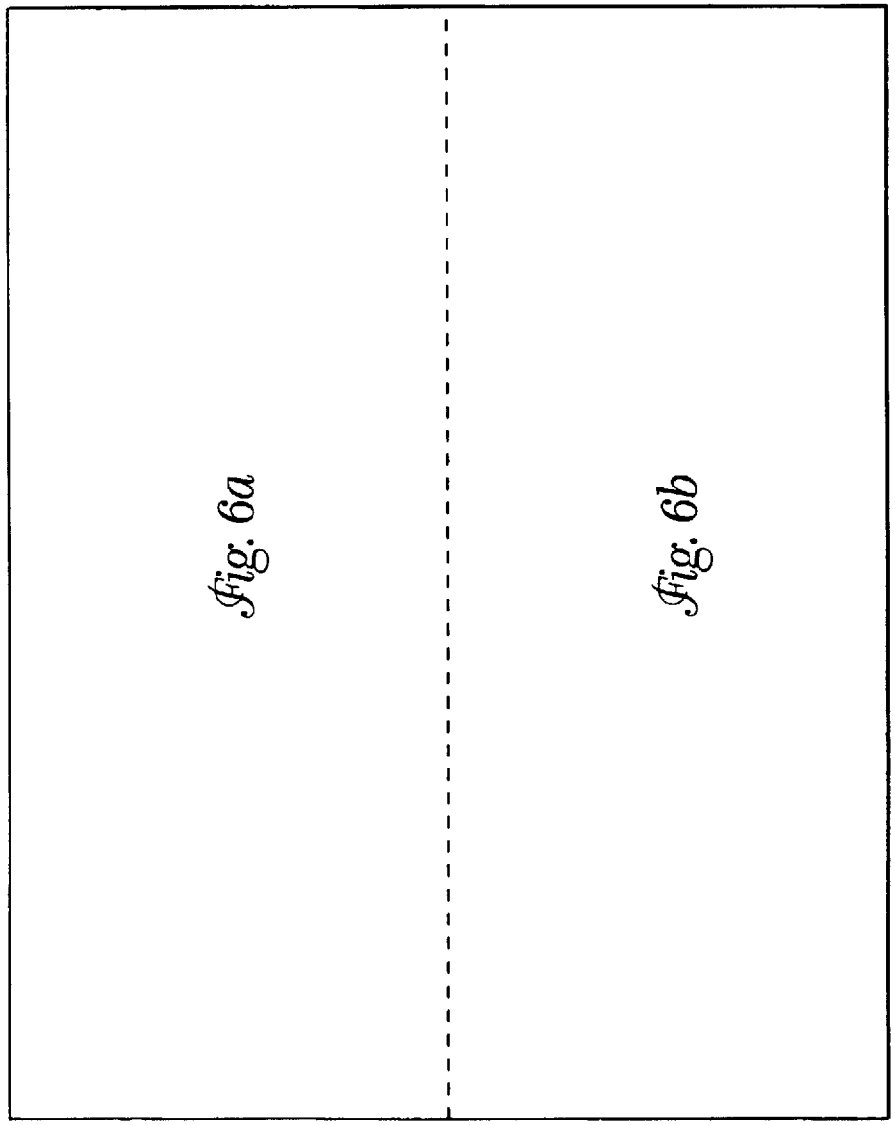

Fig. 6a

```
SEQ ID NO:5  S1    1 MASQALGFLHQNGLNTMKKWLIISVAVAASFASHADEGMMQPHQLP-AMADVEAKGIEHDAKSISKETEFPMN--AVISI
SEQ ID NO:6  S2    1 ------------------MRIALVAALVLTCGIATADEGQMQPYQMP-SIADKLSARGIDIPADKIADLTSYPMN--AVVGL
SEQ ID NO:7  X     1 -------------------MRFNLLSLSVLAIEITVDSTHAGEGMMVPQQLP-EIAGPLKQAGIQLSPEQISNLIGDPMG--AVVSL
SEQ ID NO:8  P1    1 ---------------MQMKLKSILLGAATILGASGVAKAHADEGMWLINENQENLDRMFELGFTILPLDSLYSFDKPSIANAVVIFG
SEQ ID NO:9  P2    1 ---------------MKKRLLILPLFAMICLCQIQAHSTLEHNYLENGFMAMREA--DELPNKDISVVLIDKUDDVIDYVKKDLKAIKDP

S1   78 GGCTASFVSPKGLVVTNHHCAYGSIQMNSTPEKNLFQDGFTIAKTFADEL PAAPGSRVYVTEDVINVIERVYAGIENKTG-
             S2   62 GYCTASFVSPQGLVVTNHHCAYKAIQYNIIKKEHNYLEQGFLATSMDKEPSAGPNERLYITEAVTDVTSDVTKDLSQDP--
             X    66 GNCTASIVSPEGLVITNHHCAYGAIQLNSTPKKNIIKEGHNAILQEDEVSAGPNARIMVLEQITDVTAQAKAALAAAGND
             P1   71 GCTGITVSDQGLIFTNHHCGYGAIQSQSTVDHDYLRDGFVSRLMG--EELPIPGLSVKYLRKILVKVIDKVEQOLKGITD-
             P2   67 GGCIGEVLSDRGLVLINHHCGYDMLQAHSTLEHNYLENGFMAMREA--DELPNKDISVVLIDKUEDVIDYVKKDLKAIKDP

S1  157 --------REFYQGVENQEKAIVAECEKQEGYRQQMYSFHGGLEVYLEVKQLFTRDVRLKVYNPAGSVGKYGGDVDNWMWPRHT
             S2  140 --------LKRYEELENHSKALHKSCFADDNYRCNVRSFHNGLEVYLLIKQLMIRDVRLLYIIKOMFTRNEEIKDVRLVYAPPESVGGYGGIIDNYEYPRHS
             X    146 --------PFKRITALETFSKQEHAKCEFHQGYRQOFFSFAGGNIYRVFKNIEEIKDVRLVYAPQGSVGKFGGDVDNWMWPRHT
             P1   149 --------EMEFLRKAQEVCQETAKKENADENQLCIVEPTYSNNEVFLIVDVFKPDVFRMVFAPPSSVGKFEAPPSSIGKFGADTDNWMWPRHI
             P2   146 NSMDYLSPKYLQKLADKKAGKNFSAKNFGLSVEIKALYKALVKALYGGNLMLMFTKKTYTDVRLVGAPPTSIGKFGADTDNWMWPRHI

S1  231 GDYSFYRAYVSFNGKPAEFSADNVPYEPKSFLIKVSAKGVSEGIDFVVAGYPGRTNRYRIATEVQNEFEMAVPEGKMLRER
             S2  214 GDFAPLRAYVGKDGKPAAFSEDNIPYTPKSYLKVYLEMYKVNADGVKAGDGVFVVAGYPGRTNRYMLTISEEKFASDWLXPTQAKRYQI
             X    221 GDFSFYRAYVGKDGKPAASFSKENIFYRPKHWLKFSDQPLGCDIFVVMVAGYPGRTNRYALVAEFENTAHMWYFIGQHFKN
             P1   224 GDFSVFRVYAGADNRPAEYSKDNKPYKPVYFAAVSMQGYKADDYAMIGFPGSIDRYLFISWGVEDRIEWENNPRIEVRGI
             P2   226 GDFSIFRIVADKNGNPAPYSEDNVPLKPKFRFFNISLGGVQENDYAMMGFPGIIHRYFFAASEMDEWKSIDNDIRIRMRDI

S1  311 FIETIKATAPEGSDERIKYESOIAGLANYAKNFTSMIEFYOKSTMLADRKALEAKTLAEMTAKIDSS---REAKYGKTLAEF
             S2  294 QIDITHEAMGQKDADIATKYAGNMASMANRMKKLNGILLAGFKATDIVGIKQQRENDFLAWLIKNPN------LNQNLISEI
             X    301 LHATIFAASKQNPDIOVKYASTLAGLNNVTSKNFDGQLDGFRRINAIGQKQSEETAVLAWLKQQGI---RGHEALAAHQTL
             P1   304 KQGIWKEAMSADQATRLKYASKYAQSANYWKNSIGMVRGLARLDVTGRKRAEERAFADMIRKNGKSAV-----YGDVLSSLE
             P2   306 RQGVMLREMLADPQIKIMYSAKYPASONAYKRAIGANWAILKTRGLFQNKQAMQDRLIAWGAKQGTP-------RYEEAVHE
```

Fig. 6b

DIPEPTIDYLPEPTIDASES AND METHODS OF USE

RELATED APPLICATIONS

This application claims the benefit of the U.S. Provisional Application No. 60/246,827, filed Nov. 8, 2000, which is incorporated by reference in its entirety.

GOVERNMENT FUNDING

The present invention was made with government support under Grant No. DE 09761, awarded by the National Institutes of Health. The Government may have certain rights in this invention.

BACKGROUND

*Porphyromonas gingivalis* (*P. gingivalis*), an oral anaerobic bacterium, has been implicated as a causative agent of adult type periodontitis. As an asaccharolytic organism, *P. gingivalis* is totally dependent on external sources of peptides that are necessary for its growth and proliferation. In order to fulfill such a fastidious nutritional requirement this bacterium evolved a complex system of proteolytic enzymes which are now recognized as important virulence factors in the development of periodontal disease (Travis et al., *J. Adv. Exp. Med. Biol.*, 477:455–65 (2000)). The best known and well characterized enzymes of this system are gingipains R and K, arginine and lysine specific, cysteine proteinases (Curtis et al., *J. Periodontal Res.*, 34:464–72 (1999)). Working in concert with the proteinases periodontain (Nelson et al., *J. Biol. Chem.*, 274:12245–51 (1999)), collagenases/gelatinases (Birkedal-Hansen et al., *J. Periodontal Res.*, 23:258–64 (1988); Lawson et al., *Infect. Immun.*, 60:1524–29 (1992); Kato et al., *J. Bacteriol.*, 174:3889–95 (1992), prtT (Otogoto et al., *Infect. Immun.*, 61:117–23 (1993)), and Tpr (Bourgeau et al., *Infect. Immun.*, 60:3186–92 (1992)) as well as host proteinases, this array of enzymes has the potential to degrade proteins from both the periodontal ligamentum and surrounding tissues. Their concerted action leads to the formation of a large pool of oligopeptides, which can be further utilized by *P. gingivalis* and other oral bacteria. However, *P. gingivalis* cannot transport poly- and oligo-peptides into the cell, even though it has the ability to thrive on dipeptides as a sole source of carbon. This has led to an interest in studying a specialized group of *P. gingivalis* peptidases capable of hydrolyzing oligopeptides to di- and tripeptides, which can be subsequently metabolized by this periodontopathogen. The purification, characterization and cloning of prolyl tripeptidylpeptidase A (PtpA), an enzyme which liberates tripeptides from the N-terminal regions of substrates containing proline residues in the third position has been previously reported (Banbula et al., *J. Biol. Chem.*, 274:9246–52 (1999)). Dipeptidylpeptidase-IV (DPP-IV), an enzyme with similar specificity, but only dipeptylpeptidase activity, has also been cloned (Kiyama et al., *Biochim. Biophys. Acta*, 1396:39–46 (1998)), purified, and characterized (Kumagai et al., *Infect. Immun.*, 68:716–24 (2000); Banbula et al., *Infect. Immun.*, 68:1176–82 (2000)). Together with a recently described angiotensinogen-converting enzyme analogue (Awano et al., *FEBS Lett.*, 460:139–44 (1999)) all of these proteases can hydrolyze peptide bonds containing proline residues. In addition, the *P. gingivalis* genome contains three further putative coding sequences encoding proteinases homologous with dipeptidylpeptidase-IV, although their activities have not yet been identified (Banbula et al., *J. Biol. Chem.*, 274:9246–52 (1999)).

SUMMARY OF THE INVENTION

In one aspect, the present invention provides an isolated dipeptidylpeptidase, active analog, active fragment, or active modification thereof having amidolytic activity for cleavage of a peptide bond between the second and third amino acids from the N-terminal end of a target polypeptide, wherein the target polypeptide has an aliphatic or an aromatic residue as a substituent on the α-carbon atom of the second amino acid from the N-terminal end of the polypeptide. Preferably, the dipeptidylpeptidase is isolated from *Porphyromonas gingivalis*. Preferably, the dipeptidylpeptidase is a serine protease. Preferably, the dipeptidylpeptidase includes an amino acid sequence selected from the group consisting of SEQ ID NO:2, SEQ ID NO:3, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26. Preferably the dipeptidylpeptidase is encoded by a nucleic acid including a nucleotide sequence SEQ ID NO:1.

In another aspect, the present invention provides an isolated polypeptide including an amino acid sequence having a percentage amino acid identity greater than about 40% with SEQ ID NO:2.

In another aspect, the present invention provides an isolated nucleic acid including a coding sequence encoding a dipeptidylpeptidase, active analog, active fragment, or active modification thereof having amidolytic activity for cleavage of a peptide bond between the second and third amino acids from the N-terminal end of a target polypeptide, wherein the target polypeptide has an aliphatic or an aromatic residue as a substituent on the α-carbon atom of the second amino acid from the N-terminal end of the polypeptide. Preferably the nucleic acid includes a nucleotide sequence SEQ ID NO:1. Alternatively, the complement of the nucleic acid preferably hybridizes to SEQ ID NO:1 under hybridization conditions of 0.5 M phosphate buffer, pH 7.2, 7% SDS, 10 mM EDTA, at 68° C., followed by three for 20 minutes washes in 2×SSC, and 0.1% SDS, at 65° C., wherein at least about 20 nucleotides of the complement hybridize.

In another aspect, the present invention provides an isolated nucleic acid encoding a polypeptide, wherein the polypeptide includes an amino acid sequence having a percentage amino acid identity greater than about 40% with SEQ ID NO:2.

In another aspect, the present invention provides a method of identifying an inhibitor of a dipeptidylpeptidase, active analog, active fragment, or active modification thereof. The method includes identifying a compound that inhibits the amidolytic activity of the dipeptidylpeptidase by incubating the dipeptidylpeptidase with the compound under conditions that promote amidolytic activity of the dipeptidylpeptidase and determining if the amidolytic activity of the dipeptidylpeptidase is inhibited relative to the amidolytic activity in the absence of the compound.

In another aspect, the present invention provides a method of reducing growth of a bacterium including inhibiting a dipeptidylpeptidase, active analog, active fragment, or active modification thereof, by contacting the dipeptidylpeptidase with an inhibitor of the dipeptidylpeptidase. Preferably the dipeptidylpeptidase is a serine protease.

In another aspect, the present invention provides a method for protecting an animal from a periodontal disease caused by *Porphyromonas gingivalis* including administering to the animal an inhibitor of dipeptidylpeptidase, wherein the disease is selected from the group consisting of gingivitis and periodontitis. Preferably the inhibitor is administered by a method selected from the group consisting of subgingival application and controlled release delivery.

In another aspect, the present invention provides an immunogenic composition including an isolated dipeptidylpeptidase, an antigenic analog, an antigenic fragment, or an antigenic modification thereof having amidolytic activity for cleavage of a peptide bond present in a target polypeptide, the peptide bond being located between the second and third amino acids from the N-terminal end of the target polypeptide, wherein the second amino acid from the N-terminal end has an aliphatic or an aromatic residue as a substituent on the α-carbon atom. Preferably the dipeptidylpeptidase is a serine protease. Preferably the second amino acid is selected from the group consisting of alanine, phenylalanine, isoleucine, and leucine. The immunogenic composition may optionally include an adjuvant.

In another aspect, the present invention provides a composition including an inhibitor of an isolated dipeptidylpeptidase and a pharmaceutically acceptable carrier.

Definitions

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations, and the like. A polypeptide can be produced by an organism, or produced using recombinant techniques, or chemically or enzymatically synthesized.

"Polynucleotide" and "nucleic acid" are used herein interchangeably and refer to a linear polymeric form of nucleotides of any length, either ribonucleotides or deoxynucleotides, and include both double- and single-stranded DNA and RNA. A nucleic acid may include both coding and non-coding regions that can be obtained directly from a natural source (e.g., a microorganism), or can be prepared with the aid of recombinant or synthetic techniques. A nucleic acid may be equivalent to this nucleic acid or it can include, in addition, one or more other polynucleotides. For example, the nucleic acid of the invention can be a vector, such as an expression of a coding sequence.

"Peptidase," "proteinase," and "protease" all refer to enzymes that catalyze the hydrolysis of peptide bonds in a polypeptide. A "peptide bond" or "amide bond" is a covalent bond between the alpha-amino group of one amino acid and the carboxyl group of another amino acid. "Peptidase inhibitor," "proteinase inhibitor," "protease inhibitor," and "inhibitor" all refer to compounds that inhibit a peptidase that catalyzes the hydrolysis of peptide bonds in a polypeptide.

"Serine protease" refers to an enzyme that uses the hydroxy-functional side chain of serine as a nucleophile in a catalytic reaction.

"Amidolytic activity" refers to the ability of a polypeptide to catalyze the hydrolysis of at least one peptide bond in a polypeptide. The term "cleavage" can also be used to refer to the hydrolysis of a peptide bond in a polypeptide. A "dipeptidylpeptidase" is able to hydrolyze the peptide bond between the second and third amino acids from the N-terminal end of a target polypeptide including the general formula H-Xaa-Yaa-Xaa-, wherein Xaa is a natural or modified amino acid, and Yaa is an amino acid including an aliphatic or an aromatic residue as a substituent on the α-carbon atom. Preferred amino acids in the Yaa position include alanine, phenylalanine, isoleucine, and leucine.

A "target polypeptide" is a polypeptide that is the potential substrate of the amidolytic activity of a dipeptidylpeptidase. A "dipeptidylpeptidase" does not have to cleave all members of the target polypeptide. The term "natural amino acid" refers to the 20 amino acids typically produced by a cell. The term "modified amino acid" refers to, for instance, acetylation, hydroxylation, methylation, amidation, or the attachment of carbohydrate or lipid moieties, cofactors, and the like.

As used herein, the term "isolated" means that a polypeptide or a polynucleotide has been either removed from its natural environment, produced using recombinant techniques, or chemically or enzymatically synthesized. Preferably, the polypeptide or polynucleotide is purified, i.e., essentially free from any other polypeptides, polynucleotides, and associated cellular products or other impurities.

An active analog, active fragment, or active modification of a polypeptide of the invention is one that has amidolytic activity by hydrolysis of a peptide bond present in the target polypeptide as described herein. Active analogs, active fragments, and active modifications are described in greater detail herein.

An antigenic analog, antigenic fragment, or antigenic modification of a polypeptide of the invention is one that has amidolytic activity by hydrolysis of a peptide bond present in the target polypeptide as described herein. Antigenic analogs, antigenic fragments, and antigenic modifications are described in greater detail herein.

"Percentage amino acid identity" refers to a comparison of the amino acids of two polypeptides as described herein.

As used herein, "aliphatic residue" means an organic radical having carbon atoms linked in open chains.

As used herein, "aromatic residue" means an organic radical that includes an aromatic ring (e.g., an aromatic group, an alkaryl group, or an aralkyl group).

As used herein, the "P1" position of a polypeptide is the amino acid on the N-terminal end of the scissile bond that is being cleaved. For dipeptidylpeptidases that cleave the peptide bond between the second and third amino acids from the N-terminal end of a target polypeptide, the P1 position is the second amino acid from the N-terminal end of the target polypeptide (i.e., the penultimate position).

BRIEF DESCRIPTION OF THE FIGURES

FIG. 1(*a*) illustrates the separation of DPP-7 on hydroxyapatite (100 ml) equilibrated with 20 mM potassium phosphate buffer, pH 7.0, and using a potassium phosphate gradient from 20 mM to 300 mM. FIG. 1(*b*) illustrates the separation of DPP-7 obtained from the previous step on Phenyl-Sepharose HP (25 ml) equilibrated with 50 mM potassium phosphate, 1M ammonium sulfate, pH 7.0, at a flow rate of 30 ml/hour, and using an ammonium sulfate gradient from 0.4M to 0 M. FIG. 1(*c*) illustrates the separation of DPP-7 on a MonoS FPLC column using a sodium chloride gradient from 0M to 0.3M then from 0.3M to 1M.

FIG. 5 is a listing of sequences comparing the C-terminal regions of the P. gingivalis DPP-7 (residues 664–695; SEQ ID NO:3) and S. aureus V8 endopeptidase (residues 704–863; SEQ ID NO:4). Common residues are indicated by the single letter amino acid in the line between the two sequences. The "+" symbol in the line between the two sequences indicates similar residues.

FIG. 6 depicts a multiple sequence alignment of P. gingivalis DPP-7 and its putative homologues. Sequences of DPP-7 related proteinases were obtained from the conceptual translation of the following ORFs retrieved from unfinished and finished genomes databases (available at www.tigr.org): S1-Shewanella putrefaciens gnl | TIGR_24 | sputre 6401 (SEQ ID NO:5); S2-Shewanella putrefaciens gnl | TIGR_24| sputre 6410 (SEQ ID NO:6); X-Xylella fastidiosa gb | AE004008.1 | (SEQ ID NO:7); P1-Porphyromonas gingivalis gnl | TIGR | P. gingivalis_ CPG.con (SEQ ID NO:8); P2- P. gingivalis DPP-7 gnl | TIGR | P. gingivalis CPG.con (SEQ ID NO:9). The sequences were subsequently aligned using the ClustalW multiple sequence alignment tool.

DETAILED DESCRIPTION OF THE PREFERRED EMBODIMENTS

Figure 1A:
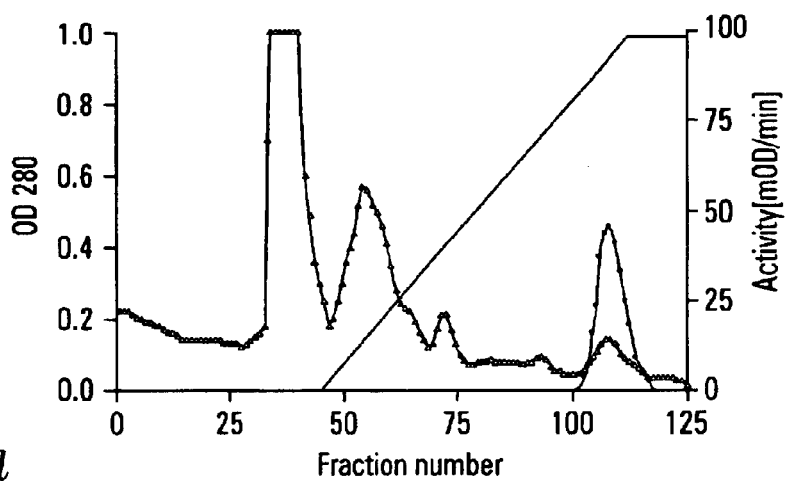
FIG. 1 depicts a plot of the absorbance at 280 nm (Δ) and amidolytic activity against Ala-Phe-pNA (●) for the purification of *P. gingvivalis* dipeptidylpeptidase (DPP-7) from the acetone precipitate of the *P. gingivalis* cell extract. The straight solid lines indicate gradients in the eluting composition.

The present invention provides isolated polypeptides, preferably isolated dipeptidylpeptidases, that have amidolytic activity by hydrolysis of a peptide bond present in a target polypeptide, wherein the bond is between the second and third amino acid from the N-terminus of the peptide. The dipeptidylpeptidase has amidolytic activity by hydrolysis of a peptide bond present in a target polypeptide including the fragment H-Xaa-Yaa-Xaa-, wherein Xaa is a natural or modified amino acid, Yaa is an amino acid including an aliphatic or an aromatic residue as a substituent on the α-carbon atom, and the peptide bond of the target polypeptide that is hydrolyzed is the bond between the second and third amino acids from the N-terminus of the peptide. In increasing order of preference, isolated polypeptides can cleave a target polypeptide that is at least about 5 amino acids or at least about 400 Da, at least about 10 amino acids or at least about 750 Da, at least about 20 amino acids or at least about 1,500 Da, or at least about 30 amino acids or at least about 3,000 Da. Preferably, the dipeptidylpeptidases cleave peptides including a sequence of H-Xaa-Yaa-Xaa-, wherein Yaa is alanine, phenylalanine, isoleucine, or leucine. More preferably, the dipeptidylpeptidases cleave peptides including a sequence of SEQ ID NO:10, SEQ ID NO:11; SEQ ID NO:12; or SEQ ID NO:13 as shown in Table 3.

The polypeptides disclosed in the present application are preferably dipeptidylpeptidases. Preferably, the dipeptidylpeptidase is isolated from Porphyromonas gingivalis. Preferably, the dipeptidylpeptidase is a serine protease. Most preferably, the dipeptidylpeptidase is P. gingivalis dipeptidylpeptidase-7 (DPP-7). The polypeptides can be used as a source of antibodies for inhibiting the amidolytic activity and thereby possibly reducing periodontitis, loss of tooth attachment and periodontal pocket formation. Antibodies to dipeptidylpeptidases can also be used to identify and/or isolate additional dipeptidylpeptidases. Knowledge of dipeptidylpeptidases can also be used to make inhibitors of dipeptidylpeptidases and to make immunogenic compositions that could be used to elicit the production of antibodies to dipeptidylpeptidases and thereby possibly reduce gingivitis, periodontitis, loss of tooth attachment, and/or periodontal pocket formation.

Dipeptidylpeptidase-7, either alone or in a mixture with other dipeptidylpeptidases, can be used to generate a pool of dipeptides from polypeptides. Dipeptides may be preferably imported by cells. Thus, pools of didpeptides might be useful substrates for transport.

Dipeptidylpeptidase-7 (DPP-7) was purified from the membrane fraction of Porphyromonas gingivalis. This enzyme, preferably having an apparent molecular mass of about 76 kDa, has specificity for polypeptides having either an aliphatic or an aromatic residue as a substituent on the α-carbon atom of the second amino acid from the N-terminal end of the polypeptide. Although it belongs to the serine class of peptidases, it does not resemble other known dipeptidylpeptidases. Interestingly, the amino acid sequence around the putative active site serine residue shows significant homology to the C-terminal region of the Staphylococcus aureus V-8 endopeptidase. In P. gingivalis, DPP-7 probably serves nutritional functions by providing dipeptides to this assaccharolytic bacterium.

Several studies indicate that the outer membrane of P. gingivalis contains a complex, proteolytic machinery which serves multiple physiological functions. The present application discloses the identification of a novel proteinase localized on the bacterial surface.

The purified enzyme migrated as a single band of about 76 kDa on SDS-PAGE and its amino-terminal sequence was located within the primary structure of the translated product of the dpp-7 coding sequence. Apparently, the enzyme is truncated at the amino terminus (i.e., amino acid 24 of SEQ ID NO:2 is the first amino acid of the truncated form) due to the action of a lysine specific proteinase, most likely gingipain K. Taking into account that the N-terminus of DPP-7 contains membrane anchorage domains it is likely that the N-terminal truncation noted here occurred during the isolation procedure and may not represent its true membrane form.

The dipeptidylpeptidases of the present invention are preferably serine proteases that are inhibited by serine protease inhibitors. The dipeptidylpeptidases of the present invention are preferably inhibited by serine protease inhibitors including, for example, diisopropylfluorophosphate (DFP), 4-(2-aminoethyl)-benzenesulfonyl fluoride hydrochloride (PEFABLOCK), and phenylmethanesulfonyl fluoride (PMSF). In addition, the dipeptidylpeptidases of the present invention are resistant to sulfhydryl group blocking reagents and chelating agents, which is also consistent with the enzyme being a serine protease. However, the P. gingivalis DPP-7 does not belong to any of the six previously described types of dipeptidylpeptidases (Barrett et al., Handbook of *Proteolytic Enzymes*, Academic Press, London (1998)). DPP-I is a member of a cysteine class of peptidases and possesses a broad specificity, but has an exclusion for basic amino acid and proline residues in the P1 site of the scissile peptide bond (McGuire et al., *Arch. Biochem. Biophys.*, 295:280–88 (1992)). DPP-VI is another representative of the cysteine proteinase family with dipeptidylpeptidase activity towards broad spectrum of substrates (Vacheron et al., *Eur. J. Biochem.*, 100:189–96 (1979)). DPP-II, DPP-IV and DPP-V belong to the S9 family of the serine proteases (Barrett et al., *Handbook of Proteolytic Enzymes*, Academic Press, London (1998)). Both DPP-II and DPP-IV share similar specificity directed against Pro and Ala residues in the penultimate position whereas DPP-V is an enzyme secreted by *Aspergillus fumigatus* with a unique substrate specificity limited to X-Ala, His-Ser, and Ser-Tyr dipeptides (Beauvais et al., *J. Biol. Chem.*, 272:6238–44 (1997)). DPP-III is also classified as a serine peptidase, with its action being restricted to Arg residue in the P1 position (Ellis et al., *J. Biol. Chem.*, 242:4623–29 (1967)). In terms of biochemical features, DPP-7 resembles a dipeptidyl aminopeptidase (DAP-BII), which was isolated from *Pseudomonas sp.* strain WO24, but the coding sequence of that enzyme remains unknown and does not allow a sequence comparison of these proteins (Ogasawara et al., *J. Bacteriol.*, 178:6288–95 (1996)). Because *P. gingivalis* dipeptidylpeptidase does not exhibit any significant homology to any of the dipeptidylpeptidases described so far, this enzyme has been designated DPP-7.

Interestingly the *P. gingivalis* DPP-7 displays the consensus sequence characteristic for the catalytic site of the V-8 like proteases, a group of endopeptidases cleaving after glutamic or aspartic acid residues (Carmona et al., *Nucleic Acids Res.*, 15:6757 (1987)). This region of homology is specifically located only at the C-terminal region of both proteases and includes the putative active site serine residue. Interestingly, more coding sequences encoding putative, DPP-7 related proteases in *P. gingivalis, Xylella fastidiosa* and *Shewanella putrefaciens* were identified. Based on the enzymological and coding sequence data presented above, the *P. gingivalis* DPP-7 does not belong to any of the peptidase families previously reported and should, therefore, be regarded as a prototype enzyme that defines a new family of dipeptidylpeptidases.

The invention further includes a polypeptide, preferably a dipeptidylpeptidase, that shares a significant level of primary structure (referred to as "percent identity") with SEQ ID NO:2. The level of identity is determined by aligning the two amino acid sequences (i.e., the amino acid sequence of the polypeptide and the sequence SEQ ID NO:2) such that the residues that make up the putative active site sequence (e.g., about amino acid 644 to about 653, preferably about amino acid 644 to about 658) are in register, then further aligned to maximize the number of amino acids that they have in common along the lengths of their sequences; gaps in either or both sequences are permitted in making the alignment in order to place the residues that make up the putative active site sequence (e.g., about amino acid 644 to about 653, preferably about amino acid 644 to about 658) in register and to maximize the number of shared amino acids, although the amino acids in each sequence must nonetheless remain in their proper order. Preferably, two amino acid sequences are compared using the blastp program of the BLAST search algorithm, which is described by Altshul et al., (*Nucl. Acids Res.*, 25, 3389–3402 (1997)), and available at the National Center for Biotechnology Information (e.g., www.ncbi.nlm.nih.gov/Microb_blast/ unfinishedgenome.html or www.ncbi.nlm.nih.gov/BLAST/). Preferably, the default values for all BLAST search parameters are used. In the comparison of two amino acid sequences using the BLAST search algorithm, structural similarity is referred to as "identities." Preferably, a dipeptidylpeptidase has, in increasing order of preference, at least about 40% identity, at least about 50% identity, at least about 60% identity, at least about 70% identity, at least about 80% identity, and most preferably at least about 90% identity with SEQ ID NO:2. Preferably, about amino acid 543 to about 699 of SEQ ID NO:2 are used, more preferably about amino acid 71 to about 712 of SEQ ID NO:2 are used. Preferably the invention includes an isolated polypeptide including an amino acid sequence having a percentage amino acid identity of greater than about 40% with SEQ ID NO:2.

In general, the amidolytic activity of the polypeptides of the invention, preferably dipeptidylpeptidases, can be measured by assay of the cleavage of a target polypeptide in the presence of dipeptidylpeptidase and a buffer. Preferably, the ratio of dipeptidylpeptidase to target polypeptide is at least about 1:1; more preferably at least about 1:100; even more preferably at least about 1:1,000; and most preferably at least about 1:10,000. Preferably, the ratio of dipeptidylpeptidase to target polypeptide is at most about 1:10,000,000; more preferably at most about 1:1,000,000; and most preferably at most about 1:100,000. Buffers in which a dipeptidylpeptidase is active are suitable for the assay. Preferably, the buffer is at most about 200 mM HEPES (4-(2-hydroxyethyl)-1-piperazineethanesulfonic acid), more preferably at most about 50 mM HEPES, and most preferably at most about 20 mM HEPES. Preferably, the pH of the buffer is at least about pH 6.0. Preferably, the pH of the buffer is at most about pH 8.0 and more preferably at most about pH 7.5. Preferably, the temperature of the assay is about 37° C. The assay can be carried out for at least about 1 minute to at most about 24 hours. Preferably, the amidolytic activity of the dipeptidylpeptidases are measured at a dipeptidylpeptidase:target polypeptide ratio of at least about 1:100 and at most about 1:1,000,000 in about 200 mM HEPES, about pH 7.5 at about 37° C. for at least about 3 hours. In general, the time of the assay can vary depending on the substrate and enzyme:substrate ratio. Typically, target polypeptides are stable under these conditions, and typically it is difficult to detect background levels of hydrolysis in the absence of a dipeptidylpeptidase. Preferably, the assay is allowed to continue until at least about 1% of the target polypeptide is hydrolyzed.

Dipeptidylpeptidases of the present invention are preferably inhibited by compounds including, for example, 4-(2-aminoethyl)-benzenesulfonyl fluoride hydrochloride (PEFABLOCK); diisopropylfluorophosphate (DFP); phenylmethanesulfonyl fluoride (PMSF); 3,4-dichloisocoumarin; and combinations thereof. The peptidases of the present invention are preferably not inhibited by a compounds including, for example, specific inhibitors of metallo peptidases, cysteine peptidases, and aspartic peptidases.

An active analog, active fragment, or active modification of a polypeptide including the amino acid sequence SEQ ID NO:2 is one that has amidolytic activity by hydrolysis of the target polypeptide described above. Active analogs of a polypeptide including the amino acid sequence SEQ ID NO:2 include dipeptidylpeptidases having amino acid substitutions that do not eliminate hydrolysis of the target polypeptide at the peptide bond between the second and third amino acids. Substitutes for an amino acid may be selected from other members of the class to which the amino acid belongs. For example, nonpolar (hydrophobic) amino acids include alanine, leucine, isoleucine, valine, proline, phenylalanine, and tryptophan. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$.

Active fragments of a dipeptidylpeptidase of the invention include dipeptidylpeptidases containing deletions or additions of one or more contiguous or noncontiguous amino acids such that the resulting polypeptide will hydrolyze the target polypeptide at the bond between the second and third amino acids. Modified dipeptidylpeptidases include dipeptidylpeptidases that are chemically and enzymatically derivatized at one or more constituent amino acid, including side chain modifications, backbone modifications, and N- and C-terminal modifications including acetylation, hydroxylation, methylation, amidation, and the attachment of carbohydrate or lipid moieties, cofactors, and the like. Modified dipeptidylpeptidases will hydrolyze the target polypeptide at the peptide bond between the second and third amino acids.

Preferably, a dipeptidylpeptidase includes the sequence TGGNSGSPV (SEQ ID NO:26), and more preferably includes the consensus sequence for the active-site serine residue of serine type proteases, TGGNSGSPVF (SEQ ID NO:25), where T is Threonine, G is glycine, N is Asparagine, P is Proline, V is valine, F is Phenylalanine, and S is serine, with the putative active site serine being underlined. The active site serine can be identified by, for instance, labeling with diisopropylfluorophosphate as described herein. Preferably, the catalytic domain of the dipeptidylpeptidases of the invention begins at about residue 543 of SEQ ID NO:2 and includes the remaining 169 amino acids, more preferably begins at about residue 540 of SEQ ID NO:2 and includes the remaining 172 amino acids, and most preferably begins at about residue 522 of SEQ ID NO:2 and includes the remaining carboxy-terminal amino acids.

Dipeptidylpeptidases can be obtained by several methods. Isolation of a dipeptidylpeptidase present on the surface of a cell producing the peptidase typically requires lysis of the cell followed by purification methods that are well known in the art. Alternatively, cells can be treated with a detergent, for instance Triton X-100, to remove the peptidase from the cell surface. The following are nonlimiting examples of suitable protein purification procedures: fractionation on immunoaffinity, ion-exchange, hydroxyapatite, Phenyl-Sepharose HP, MonoQ HR 5/5, or MonoP columns; ethanol precipitation; reverse phase HPLC; chromatography on silica or on an ion-exchange resin such as DEAE; chromato-focusing; SDS-PAGE; ammonium sulfate precipitation; gel filtration using, for example, Sephadex G-75. Preferably, isolation of a dipeptidylpeptidase from *P. gingivalis* is accomplished using a combination of hydroxyapatite, Phenyl-Sepharose HP, MonoS HR 5/5 and MonoP column chromatography steps as described herein.

Dipeptidylpeptidases can also be isolated from organisms other than *P. gingivalis*. Other organisms can express a dipeptidylpeptidase that is encoded by a coding region having similarity to the coding region encoding SEQ ID NO:2. A "coding region," a "coding sequence," or an "open reading frame" (ORF) is a linear form of nucleotides that encodes a polypeptide, usually via mRNA, when placed under the control of appropriate regulatory sequences. The boundaries of a coding region are generally determined by a translation start codon at its 5' end and a translation stop codon at its 3' end. "Regulatory region" refers to a nucleic acid that regulates expression of a coding region to which a regulatory region is operably linked. Non limiting examples of regulatory regions include promoters, transcription initiation sites, translation start sites, translation stop sites, and terminators. "Operably linked" refers to a juxtaposition wherein the components so described are in a relationship permitting them to function in their intended manner. A regulatory element is "operably linked" to a coding region when it is joined in such a way that expression of the coding region is achieved under conditions compatible with the regulatory region. Alternatively, other organisms can express a dipeptidylpeptidase from a recombinant coding region encoding the peptidase. The identification of similar coding regions in other organisms can be accomplished as described herein. A dipeptidylpeptidase can be isolated using purification methods that are well known in the art. Alternatively, the peptidase can be chemically synthesized using methods that are well known in the art including, for instance, solid phase synthesis. Examples of, for instance, coding and regulatory regions are described herein.

The expression of a dipeptidylpeptidase by an organism other than *P. gingivalis* can be detected using specific substrates of the general formula Xaa-Xaa-LG, wherein Xaa represents any natural amino acid and LG is a leaving group. The leaving group can be a chromogenic or fluorogenic group known to the art. The expression of a dipeptidylpeptidase by an organism and subsequent cleavage of a specific substrate results in a free amino acid or a free leaving group, each of which can be assayed using techniques known to those of skill in the art. Other methods can be based on immunogenic properties of DPP-7, for instance immunoassays and histochemistry, the detection of mRNA, and PCR related methods, all of which are known to one of skill in the art.

In one aspect, the present invention is directed to a nucleic acid encoding a polypeptide, particularly a dipeptidylpeptidase, active analog, active fragment, or active modification thereof. The nucleic acid can have a nucleotide sequence as shown in SEQ ID NO:1. Alternatively, nucleic acids of the invention include those whose complement hybridize to SEQ ID NO:1 under standard hybridization conditions as described herein. During hybridization the entire nucleotide sequence of the complement can hybridize with SEQ ID NO:1. Preferably, at least about 20 nucleotides of the complement hybridize with SEQ ID NO:1, more preferably at least about 50 nucleotides, most preferably at least about 100 nucleotides.

The identification of similar coding regions in other organisms can be accomplished by screening individual wild-type microorganisms for the presence of nucleotide sequences that are similar to the coding region of DPP-7, which is shown in SEQ ID NO:1. Screening methods include, for instance, hybridization of a detectably labeled probe with a nucleic acid.

Standard hybridizing conditions are a modification of the conditions used by Church et al. ((1984) *Proc. Natl. Acad. Sci. USA* 81, 1991): 0.5 M phosphate buffer, pH 7.2, 7% SDS, 10 mM EDTA, at 68° C., and three washes, each for 20 minutes in 2×SSC (preferably 0.1 SSC), 0.1% SDS, at 65° C. Preferably, a probe will hybridize to the nucleotide sequence set forth in SEQ ID NO:1 under standard hybridizing conditions. Generally the probe does not have to be complementary to all the nucleotides of the nucleic acid as long as there is hybridization under the above-stated conditions.

"Complement" and "complementary" refer to the ability of two single stranded nucleic acids to base pair with each other, where an adenine on one nucleic acid will base pair to a thymine on a second nucleic acid and a cytosine on one nucleic acid will base pair to a guanine on a second nucleic acid. Two nucleic acids are complementary to each other when a nucleotide sequence in one nucleic acid can base pair with a nucleotide sequence in a second nucleic acid. For instance, 5'-ATGC and 5'-GCAT are complementary. The term complement and complementary also encompasses two nucleic acids where one nucleic acid contains at least one nucleotide that will not base pair to at least one nucleotide present on a second nucleic acid. For instance the third nucleotide of each of the two nucleic acids 5'-ATTGC and 5'-GCTAT will not base pair, but these two nucleic acids are complementary as defined herein. Typically two nucleic acids are complementary if they hybridize under the standard conditions referred to herein.

Preferred probes are nucleic acids complementary to a coding region or another nucleotide sequence that encodes a dipeptidylpeptidase. For instance, a probe can include a consecutive series of nucleotides complementary to a portion of SEQ ID NO:1. Preferably a probe is at least about 18 bases, more preferably at least about 21 bases, and most preferably at least about 24 bases in length. One of skill in the art could select useful probes as desired. Methods of detectably labeling a probe are well known to the art.

The nucleic acid that is identified by the probe is further analyzed to determine if it encodes a polypeptide with amidolytic activity of the peptide bond between the second and third amino acids from the N-terminus on a target polypeptide of the general formula H-Xaa-Yaa-Xaa, wherein Xaa is a natural or modified amino acid and Yaa is an amino acid including an aliphatic or an aromatic residue as a substituent on the α-carbon atom. Another method for screening individual microorganisms for the presence of nucleotide sequences that are similar to the coding regions of the present invention is the polymerase chain reaction (PCR).

Individual wild-type microorganisms containing nucleic acids encoding a dipeptidylpeptidase can also be identified using antibody. Preferably the antibody is directed to DPP-7. The production of antibodies to a particular polypeptide is known to a person of skill in the art, and is further detailed herein.

The use of hybridization of a probe to a coding region present in individual wild-type microorganisms can be used as a method to identify a coding region identical or similar to a coding region present in SEQ ID NO:1. The coding region can then be isolated and ligated into a vector as described below.

The present invention is also directed to coding regions sharing a significant level of primary structure with the coding region present at SEQ ID NO:1. The level of identity is determined by aligning the two nucleotide sequences (i.e., the nucleotide sequence of the polynucleotide and the sequence SEQ ID NO:1) such that the residues that encode the putative active site of the encoded protein (e.g., about nucleotide 1929 to about 1974) are in register, then further aligned to maximize the number of nucleotides that they have in common along the lengths of their sequences; gaps in either or both sequences are permitted in making the alignment in order to place the residues that encode the putative active site of the encoded protein (e.g., about nucleotide 1929 to about 1974) in register and to maximize the number of shared nucleotides, although the nucleotides in each sequence must nonetheless remain in their proper order. Preferably, two nucleotide sequences are compared using the blastn program of the BLAST search algorithm, which is described by Altshul et al., (Nucl. Acids Res., 25, 3389–3402 (1997)), and available at the National Center for Biotechnology Information (e.g., www.ncbi.nlm.nih.gov/Microb_blast/unfinishedgenome.html or www.ncbi.nlm.nih.gov/BLAST/). Preferably, the default values for all BLAST search parameters are used. In the comparison of two nucleotide sequences using the BLAST search algorithm, structural similarity is referred to as "identities." Preferably, two nucleotide acid sequences have, in increasing order of preference, preferably at least about 70%, at least about 80%, at least about 90%, at least about 95%, and most preferably at least about 95% identity.

As mentioned above, a nucleic acid of the invention can be inserted in a vector. Construction of vectors containing a nucleic acid of the invention employs standard ligation techniques known in the art. See, e.g., Sambrook et al, *Molecular Cloning: A Laboratory Manual.*, Cold Spring Harbor Laboratory Press (1989) or Ausubel, R. M., ed. *Current Protocols in Molecular Biology* (1994). A vector can provide for further cloning (amplification of the nucleic acid), i.e., a cloning vector, or for expression of the polypeptide encoded by the coding region, i.e., an expression vector. The term vector includes, but is not limited to, plasmid vectors, viral vectors, cosmid vectors, or artificial chromosome vectors. Typically, a vector is capable of replication in a bacterial host, for instance *E. coli*. Preferably the vector is a plasmid.

Selection of a vector depends upon a variety of desired characteristics in the resulting construct, such as a selection marker, vector replication rate, and the like. Suitable plasmids for expression in *E. coli*, for example, include pUC(X), pKK223-3, pKK233-2, pTrc99A, and pET-(X) wherein (X) denotes a vector family in which numerous constructs are available. pUC(X) vectors can be obtained from Pharmacia Biotech (Piscataway, N.H.) or Sigma Chemical Co. (St. Louis, Mo.). pKK223-3, pKK233-2 and pTrc99A can be obtained from Pharmacia Biotech. pET-(X) vectors can be obtained from Promega (Madison, Wis.) Stratagene (La Jolla, Calif.) and Novagen (Madison, Wis.). To facilitate replication inside a host cell, the vector preferably includes an origin of replication (known as an "ori") or replicon. For example, ColE1 and P15A replicons are commonly used in plasmids that are to be propagated in *E. coli*.

An expression vector optionally includes regulatory regions operably linked to the coding region. The invention is not limited by the use of any particular promoter, and a wide variety are known. Promoters act as regulatory signals that bind RNA polymerase in a cell to initiate transcription of a downstream (3' direction) coding region. The promoter used in the invention can be a constitutive or an inducible promoter. It can be, but need not be, heterologous with respect to the host cell. Preferred promoters for bacterial transformation include lac, lacUV5, tac, trc, T7, SP6 and ara.

An expression vector can optionally include a Shine Dalgamo site (e.g., a ribosome binding site), and a start site (e.g., the codon ATG) to initiate translation of the transcribed message to produce the enzyme. It can also include a termination sequence to end translation. A termination sequence is typically a codon for which there exists no corresponding aminoacetyl-tRNA, thus ending polypeptide synthesis. The nucleic acid used to transform the host cell can optionally further include a transcription termination sequence. The rrnB terminators, which is a stretch of DNA that contains two terminators, T1 and T2, is an often used terminator that is incorporated into bacterial expression systems (J. Brosius et al., (1981) *J. Mol. Biol.* 148 107–127).

The nucleic acid used to transform the host cell optionally includes one or more marker sequences, which typically encode a polypeptide that inactivates or otherwise detects or is detected by a compound in the growth medium. For example, the inclusion of a marker sequence can render the transformed cell resistant to an antibiotic, or it can confer compound-specific metabolism on the transformed cell. Examples of a marker sequence are sequences that confer resistance to kanamycin, ampicillin, chloramphenicol, and tetracycline.

Antibodies to a polypeptide including the sequence SEQ ID NO:2 can be produced. Alternatively, antibodies to an antigenic analog, antigenic fragment, or antigenic modification of a polypeptide including the sequence SEQ ID NO:2 can be made. An antigenic analog, antigenic fragment, or antigenic modification of a polypeptide including the amino acid sequence SEQ ID NO:2 is one that generates an immune response in an animal. Preferably, an antigenic analog, antigenic fragment, or antigenic modification has amidolytic activity. Antigenic analogs of a polypeptide including the amino acid sequence SEQ ID NO:2 include dipeptidylpeptidases having amino acid substitutions that do not eliminate peptide antigenicity in an animal. Substitutes for an amino acid may be selected from other members of the class to which the amino acid belongs, as described herein. Fragments of a dipeptidylpeptidase of the invention include dipeptidylpeptidases containing deletions or additions of one or more contiguous or noncontiguous amino acids such that the resulting polypeptide will generate an immune response in an animal. Modified dipeptidylpeptidases include dipeptidylpeptidases that are chemically and enzymatically derivatized at one or more constituent amino acids, including side chain modifications, backbone modifications, and N- and C-terminal modifications including acetylation, hydroxylation, methylation, amidation, and the attachment of carbohydrate or lipid moieties, cofactors, and the like.

Accordingly, an aspect of the invention is an immunogenic composition including an isolated dipeptidylpeptidase, an antigenic analog, antigenic fragment, or antigenic modification thereof. The dipeptidylpeptidase preferably has amidolytic activity for cleavage of the target polypeptide described herein.

The immunogenic composition can further include excipients or diluents that are pharmaceutically acceptable as carriers and compatible with the immunogenic composition. The term "pharmaceutically acceptable carrier" refers to a carrier(s) that is "acceptable" in the sense of being compatible with the other ingredients of a composition and not deleterious to the recipient thereof. Suitable excipients include, for example, water, saline, dextrose, glycerol, ethanol, and combinations thereof. In addition, if desired, the immunogenic composition may contain minor amounts of auxiliary substances such as wetting or emulsifying agents, pH buffering agents, and/or adjuvants which enhance the effectiveness of the immune-stimulating composition.

The immunogenic composition can be used in a method for protecting an animal from a disease caused by *P. gingivalis*. This method includes administering the immunogenic composition and eliciting antibodies to a dipeptidylpeptidase, antigenic analog, antigenic fragment, or antigenic modification. The diseases that can be treated in this manner include periodontal diseases, which include gingivitis and periodontitis. Clinical hallmarks of periodontitis include loss of tooth attachment and periodontal pocket formation.

Alternatively and preferably, periodontal diseases can be treated by the use of inhibitors of a dipeptidylpeptidase. An inhibitor of a dipeptidylpeptidase can be present in a composition that preferably contains a pharmaceutically acceptable carrier. For instance, inhibitors can be applied systemically, subgingivally (e.g., subgingival irrigation), and/or by controlled release delivery directly into the periodontal pocket using methods well known in the art (see, e.g., Kornman, *J. Periodontol.* 64:782–91 (1993). Preferably, an inhibitor is applied subgingivally or by controlled release delivery.

The dipeptidylpeptidases, active analogs, active fragments, and active modifications thereof can be used in a method of reducing growth of bacteria in vitro or in vivo. Preferably, the bacteria is a periodontal pathogen, i.e, a bacterial pathogen that causes periodontal disease, more preferably the bacteria is *P. gingivalis*. The inability of asaccharolytic *P. gingivalis* to utilize free amino acids makes the bacterium entirely dependant on an external peptide supply. The action of the polypeptides of the invention may be required for bacterial growth, and inhibition of the polypeptides of the invention may inhibit the in vivo growth of organisms, including *P. gingivalis*. The method includes decreasing the amount of dipeptides (e.g., the result of cleavage of the target polypepitde by a dipeptidylpeptidase) and the amount of free amino acids that result from further cleavage of the dipeptides present by inhibiting a dipeptidylpeptidase, active analog, active fragment, or active modification thereof, such that the amount of dipeptides generated by the polypeptides is decreased. The amount of dipeptides is decreased relative to the amount of dipeptides present in the absence of the inhibitor. Preferably, the amount of dipeptides generated is decreased by an inhibitor, a monoclonal antibody that inhibits the dipeptidylpeptidase, or polyclonal antibodies that inhibit the dipeptidylpeptidase, more preferably, the amount of dipeptides generated is decreased by an inhibitor. Preferably, an inhibitor acts to inhibit a polypeptide of the invention, preferably a dipeptidylpeptidase, by blocking the active site of the polypeptide. The polypeptide can be present on the surface of the bacteria or secreted into the environment, preferably the polypeptide is present in the surface of the bacteria.

The present invention is also directed to a method of developing an inhibitor of a dipeptidylpeptidase, active analog, active fragment, or active modification thereof, preferably a dipeptidylpeptidase. The method includes identifying a compound that inhibits the amidolytic activity of the dipeptidylpeptidase. Such compounds include, for example, polypeptides, organic compounds, inorganic compounds, metals, non-ribosomal polypeptides, polyketides, and peptidomimetics. The identification of compounds can be accomplished by, for instance, incubating the dipeptidylpeptidase with a candidate compound under conditions that promote amidolytic activity of the dipeptidylpeptidase and determining if the amidolytic activity of the dipeptidylpeptidase is decreased relative to the amidolytic activity in the absence of the compound. The amidolytic activity can be measured by cleavage of the peptide bond between the second and third amino acids of the target polypeptide as described herein. One method of developing an inhibitor includes using the target polypeptide and replacing the Xaa residues with modified amino acids. It is expected that some modified amino acids will cause the target polypeptide to act as an inhibitor.

The present invention is illustrated by the following examples. It is to be understood that the particular examples, materials, amounts, and procedures are to be interpreted broadly in accordance with the scope and spirit of the invention as set forth herein.

EXAMPLES

Materials

Diisopropylfluorophosphate (DFP), leupeptin and 3,4-dichloroisocoumarin, were purchased from Calbiochem (La Jolla, Calif.). Other peptides used in this study were synthesized at the Molecular Genetic Instrumental Facility (University of Georgia, Athens, Ga.) using Fmoc protocol with an advanced ChemTech MPS350 automated synthesizer. The peptides H-Xaa-Xaa-pNA and Z-Xaa-Xaa-pNA, where pNA is p-Nitroanilide; Z is benzyloxycarbonyl; and H is hydrogen and denotes an unblocked amino-terminal group were obtained from Bachem (King of Prussia, Pa.).

Methods

Example 1

Source and Cultivation of Bacteria—*P. gingivalis* DPP-7 was purified from strain HG66, a kind gift of Dr. Roland Arnold (University of North Carolina, Chapel Hill, N.C.). The cells were grown as described previously (Chen et al., *J. Biol. Chem.*, 267:18896–901 (1992)).

Protein Determination—Protein concentration was determined with the BCA reagent kit (Sigma), using bovine serum albumin as a standard.

Localization of Dipeptidylpeptidase Activity—The localization of active enzyme was checked in bacterial cells that had been subjected to a previously described fractionation procedure (Banbula et al., *Infect. Immun.*, 68:1176–82 (2000)). All fractions, as well as the full culture, culture medium, and full culture after sonication, were assayed for amidolytic activity against H-Ala-Phe-pNA.

Enzyme Purification—All purification steps were performed at 4° C. except for FPLC separations, which were carried out at room temperature. The cells were collected by centrifugation (6,000×g, 30 minutes) and resuspended in 50 mM potassium phosphate buffer, pH 7.4. The outer membrane proteins were solubilized with 0.05% Triton X-100. After 2 hours of gentle stirring, unbroken cells were removed by centrifugation (28,000-×g, 60 minutes). Proteins from the supernatant were precipitated with cold acetone (60% final concentration), collected by centrifugation, and redissolved in 50 mM potassium phosphate buffer, pH 7.0. After extensive dialysis against the same buffer the sample was loaded onto a hydroxyapatite column (BioRad) previously equilibrated with 20 mM potassium phosphate, pH 7.0, at a flow rate of 20 ml/hour. The column was then washed until the $A_{280}$ fell to zero. Bound proteins were eluted with a potassium phosphate gradient (20–300 mM) and fractions (7 ml) were analyzed for amidolytic activity against H-Ala-Phe-pNA. The active fractions were saturated with 1 M ammonium sulfate and loaded onto a Phenyl-Sepharose HP column (Pharmacia) equilibrated with 50 mM potassium phosphate, pH 7.0, containing 1 M ammonium sulfate. The column was washed with two volumes of the equilibration buffer, followed by a wash with buffer containing 0.4 M ammonium sulfate, and developed with a descending gradient of ammonium sulfate from 0.4 to 0 M. Active fractions were pooled, extensively dialyzed against 20 mM MES, pH 6.6, and applied onto a MonoS HR 5/5 FPLC (Pharmacia) column equilibrated with the same buffer. Bound proteins were eluted with a 0–300 mM NaCl gradient. This allowed us to obtain a homogenous preparation of active proteinase.

Electrophoretic Techniques—The SDS-PAGE system of Schagger and von Jagow (Schagger et al., *Anal. Biochem.*, 166:368–79 (1987)), was used to monitor enzyme purification and estimate the enzyme molecular mass. For amino-terminal sequence analysis, proteins resolved in SDS-PAGE were electroblotted onto polyvinylidene difluoride membranes using 10 mM CAPS, pH 11, 10% methanol (Matsudaira et al., *J. Biol. Chem.*, 262:10035–38 (1987)). After staining with Coomasie Blue G250 the blot was air dried, and protein bands cut out and subjected to amino-terminal sequence analysis with an Applied Biosystems 491 Protein Sequencer using the program designed by the manufacturers.

Kinetic Analysis—Routinely, the dipeptidylpeptidase amidolytic activity was measured with H-Ala-Phe-pNA (1 mM) in 0.2 M HEPES, pH 7.8 at 37° C. The reaction was followed for specific time intervals in a thermostated ELISA reader (SpectraMax, Applied Biosystem) and the release of p-nitroaniline was monitored at 405 nm. Other p-nitroanilide substrates were used in the same manner. For inhibition studies, the enzyme was first preincubated with an inhibitor for 15 minutes at 37° C., substrate added, and residual activity recorded. The initial steady-state velocity ($v_0$) was determined by continuous assay for the range of substrate concentrations (100 nM to 1 mM). $K_m$ and $V_{max}$ were determined by hyperbolic regression of the kinetic data using the software package Hyper Version 1.02 obtained from Dr. J. S. Easterby (University of Liverpool, UK).

Enzyme Fragmentation—The purified dipeptidylpeptidase was subjected to in-gel tryptic digestion (Rosenfeld et al., *Anal. Biochem.*, 203:173–79 (1992)). Peptides were extracted and separated by microbore reverse-phase HPLC. Fractions absorbing at 210 nm were manually collected, and their masses were determined by reflectron MALDI-TOF mass spectrometry using a Bruker Daltonics ProFlex instrument as described previously (Pohl et al., *Lett. Peptide Sci.*, 1:291–97 (1995)). Selected peptides were subjected to Edman degradation in a model Procise-cLS sequencer (PE Biosystems, Calif.).

Identification of the DPP-7 Coding Sequence—An unfinished *P. gingivalis* W83 genome database, available from the Institute for Genomic Research, was searched for the presence of nucleotide sequences corresponding to the amino-terminal and the internal DPP-7 amino acid sequences using the TBLASTN algorithm (Altschul et al., *Nucleic Acids Res.*, 25:3389–402 (1997)). An identified contig gnl |TIGR | *P. gingivalis*_1208 was retrieved from the Institute for Genomic Research database. The position of the DPP-7 coding sequence was localized using the National Center for Biotechnology Information (NCBI) open reading frame (ORF) finder and the amino acid sequence, obtained by conceptual translation of the entire ORF, was further used for homology screening by use of the NCBI BLAST search tool.

Enzyme Specificity—The determination of substrate specificity was based on the separation of the products of peptide hydrolysis by reverse-phase chromatography. Peptides were first incubated with 1 microgram of DPP-7 at an enzyme: substrate molar ratio of 1:100 for 3 hours or 24 hours in 50 microliters of 200 mM HEPES, 100 mM NaCl pH 8.0, at 37° C., and the reaction stopped by acidification with trifluoroacetic acid. The samples were then subjected to reverse-phase high pressure liquid chromatography using a Supelcosil LC 18 column (Supelco) with an acetonitrile gradient 0–60% in 0.075% trifluoroacetic acid in 50 minutes. Each peak, detected at 210 nm, was collected, lyophilized, re-dissolved in 50% (v/v) methanol, 0.1% acetic acid and subjected to analysis by mass spectrometry.

Example 2

Figure 1B:
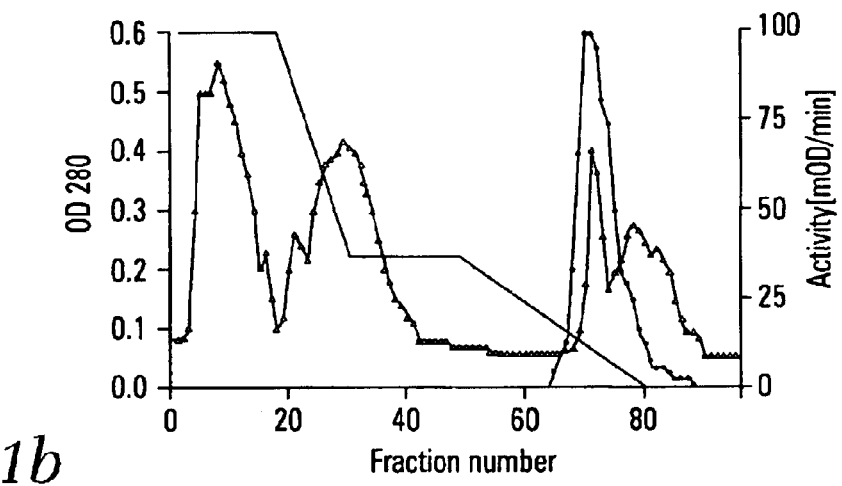
Figure 1C:
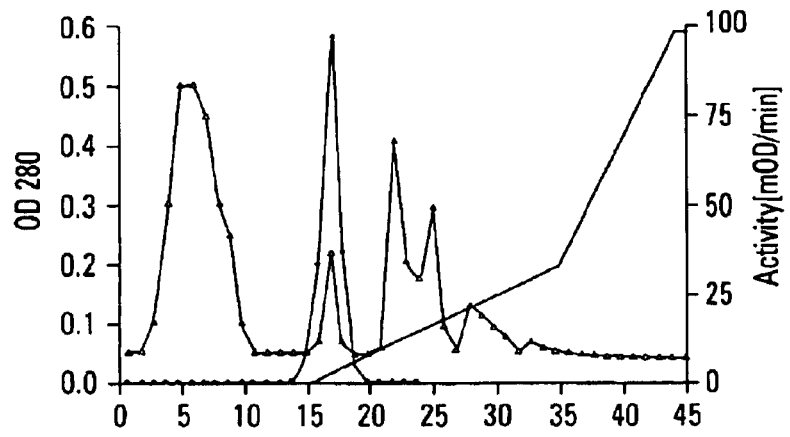
Figure 2:
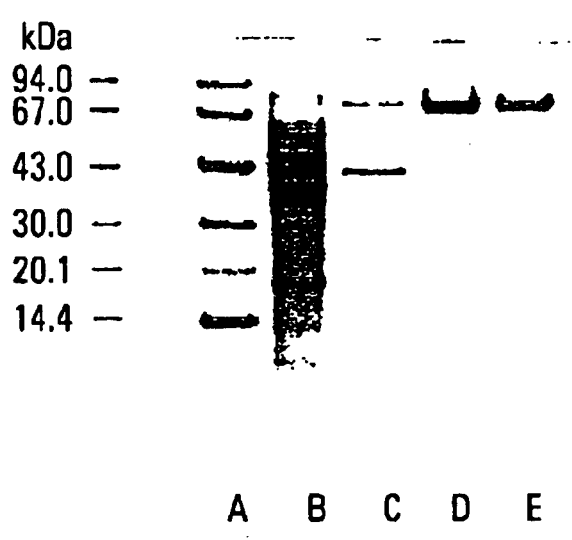
FIG. 2 is a depiction of the SDS-PAGE of fractions obtained during the purification of *P. gingivalis* DPP-7 with Lane A representing molecular mass markers (phosphorylase B, 97 kDa; bovine serum albumin, 68 kDa; ovalbumin, 43 kDa; carbonic anhydrase, 30 kDa; soybean trypsin inhibitor, 20 kDa; α-lactalbumin, 14 kDa); Lane B representing acetone precipitate from Triton X-100 extract of P. gingivalis; Lane C representing hydroxyapatite column eluate; Lane D representing Phenyl-Sepharose column eluate; and Lane E representing MonoS column eluate.

A 76 kDa dipeptidylpeptidase associated with *P. gingivalis* membranes was solubilized by mild detergent treatment. This procedure released more than 90% of the amidolytic activity against H-Ala-Phe-pNA into the medium. After acetone precipitation and subsequent chromatography steps including the use of hydroxyapatite, Phenyl-Sepharose and MonoS columns (FIG. 1) a pure enzyme preparation was obtained. The homogeneity of the preparation and molecular mass of the protein were checked both by SDS PAGE (FIG. 2) and gel filtration on a TSK G3000 SW column.

Example 3

Inhibition Profile—Based on the inhibition studies (Table I), DPP-7 was classified as a serine protease. DPP-7 was inactivated by diisopropylfluorophosphate, PEFABLOCK and 3,4-dichloisocoumarin, but not by typical cysteine class inhibitors such as E-64 or iodoacetic acid. Metal chelators including EDTA and 1,10-orthophenanthroline, as well as reducing agents did not influence its activity. The enzyme was not sensitive to inactivation by either detergents (0.5% SDS, 1% Triton X-100) or heavy metal ions including $Zn^{2+}$, $Co^{2+}$ and $Ni^{2+}$. Human plasma inhibitors, such as ($\alpha_1$-proteinase inhibitor, $\alpha_1$-antichymotrypsin, and $\alpha_2$-macroglobulin, did not effect enzyme activity nor were they cleaved by DPP-7.

TABLE I

Effect of different compounds on P. gingivalis DPP-7 activity.

| Inhibitor | Concentration | % of residual activity |
|---|---|---|
| Diisopropylfluorophosphate | 10 mM | 34 |
| PEFABLOCK | 4 mg/ml | 1 |
| 3,4-dichloroisocoumarin | 2 mM | 0 |
| E-64 | 1 micromolar | 96 |
| Iodoacetic acid | 0.1 mM | 102 |
| EDTA | 10 mM | 90 |
| 1,10-orthophenanthroline | 1 mM | 98 |
| Leupeptin | 0.1 mM | 107 |
| Aprotinin | 0.5 mg/ml | 128 |
| Pepstatin | 0.5 mg/ml | 127 |
| Cysteine | 10 mM | 90 |
| Gly-Ala | 100 mM | 102 |
| Arg-Phe | 100 mM | 69 |
| Ala-Gly | 100 mM | 96 |
| Arg-Gly | 10 mM | 84 |
| Lys-Gly | 10 mM | 96 |
| $Ni^{++}$ | 1 mM | 95 |
| $Zn^{++}$ | 1 mM | 95 |
| $Co^{++}$ | 1 mM | 116 |
| SDS | 0.5% | 65 |
| SDS | 1% | 0 |
| Triton X-100 | 0.1% | 144 |
| Triton X-100 | 0.5% | 103 |
| Triton X-100 | 1% | 94 |

Figure 3:
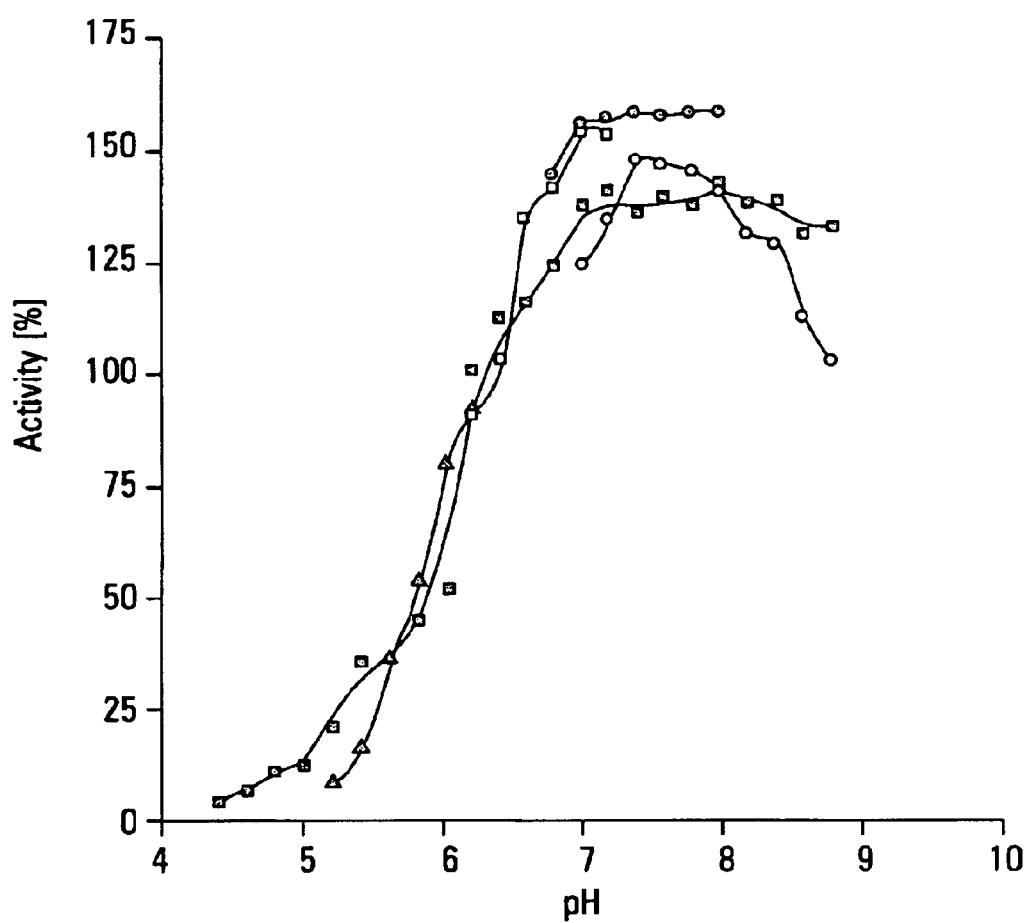
FIG. 3 depicts a plot of the DPP-7 activity against Ala-Phe-pNA vs. pH. Enzyme activity was tested on Ala-Phe-pNA substrate in different buffers including: HEPES (●); PIPES (□); potassium phosphate (■); Tris (○); and MES (▼).

Example 4 pH Optimum and Stability—Purified DPP-7 was active against H-Ala-Phe-pNA over a broad pH range, from neutral to basic pH (6.5–9.0) (FIG. 3). This activity also changed with the ionic strength of the buffer, reaching 200% at 0.5 M NaCl concentration in 100 mM HEPES, pH 8.0. DPP-7 was stable in 0.2 M HEPES, pH 8.0, for one week at 4° C. The protease showed no appreciable loss of activity when kept frozen at −80° C. for one month. After 3 hours incubation at either room temperature or 37° C., activity was reduced to 62% and 20%, respectively. The optimum temperature for the hydrolysis of H-Ala-Phe-pNA was determined to be 43° C.

Example 5

Substrate Specificity—Among several chromogenic substrates tested, only those with an aliphatic or an aromatic side chain residues in the second, penultimate position were rapidly hydrolyzed by DPP-7 (Table 2).

TABLE 2

Kinetic analysis for paranitroanalides cleavage by DPP-7.

| Substrate | Km [mM] | Vmax |
|---|---|---|
| H-Ala-Ala-pNA | 0.313 | 129.65 |
| H-Ala-Phe-pNA | 0.441 | 170.06 |
| H-Gly-Phe-pNA | 0.256 | 54.54 |

Several other substrates including H-Ala-Pro-pNA, H-Ala-pNA, H-Gly-pNA, H-Ile-pNA, H-Leu-pNA, H-Lys-pNA, H-Phe-pNA, H-Gly-Arg-pNA, H-Gly-Glu-pNA, H-Gly-Lys-pNA, H-Ala-Gly-pNA, H-Gly-Gly-pNA, H-Ala-Ala-Phe-pNA, H-Ala-Gly-Arg-pNA, H-Leu-Thr-Arg-pNA, H-Ala-Phe-Pro-pNA, Nα-benzoyl-DL-arginine-pNA, N-met-Ala-Pro-Val-pNA, N-suc-Ala-Ala-pNA, N-suc-Ala-Ala-Pro-Glu-pNA, N-suc-Ala-Ala-Pro-Leu-pNA, N-suc-Ala-Ala-Val-Ala-pNA, Z-Ala-Ala-pNA, Z-Lys-pNA, Z-Arg-pNA, Z-Glu-Glu-pNA, Z-Leu-Leu-Glu-pNA, Z-Lys-Arg-pNA, Z-Phe-Arg-pNA, Z-Phe-Val-Arg-pNA, Z-Tyr-Lys-Arg-pNA were tested, but none of these was hydrolysed by DPP-7.

To further confirm specificity, several synthetic peptides were also tested as substrates for this enzyme. Again, only those polypeptides having an amino acid with an aliphatic or an aromatic residue as a substituent on the α-carbon atom of the second amino acid from the N-terminal end of the polypeptide were cleaved (Table 3), with glycine, proline, or charged amino acids not being acceptable as the second amino acid from the N-terminal end of the polypeptide. The protease did not show any endopeptidase activity on gelatin, insulin β chain, carboxymethylated lysosyme, azocazein or type I collagen. Purified DPP-7 was devoid of any aminopeptidase activity and did not cleave model substrates with blocked amino-termini.

TABLE 3

Specificity of *P. gingivalis* DPP-7 on synthetic peptides.

| Peptides cleaved | Peptides not cleaved |
|---|---|
| Trp-Ala-↓-Gly-Gly-Asp-Ala-Ser-Gly-Glu (SEQ ID NO:10) | Trp-His-Trp-Leu-Glu-Leu-Lys-Pro-Gly-Glu-Pro-Met-Tyr (SEQ ID NO:14) |
| Ile-Ala-↓-Arg-Arg-His-Pro-Tyr-Phe-Leu (SEQ ID NO:11) | Ser-Pro-Tyr-Ser-Ser-Glu-Thr-Thr (SEQ ID NO:15) |
| Lys-Ile-↓-Ala-Gly-Tyr-His-Leu-Glu-Leu (SEQ ID NO:12) | Ala-Pro-Val-Arg-Ser-Leu (SEQ ID NO:16) |
| Phe-Leu-↓-Arg-Glu-Pro-Val-Ile-Phe-Leu (SEQ ID NO:13) | Gln-Lys-Gln-Met-Ser-Asp-Arg-Arg-Glu (SEQ ID NO:17) |

An arrow indicates cleavage site

Example 6

Figure 4:
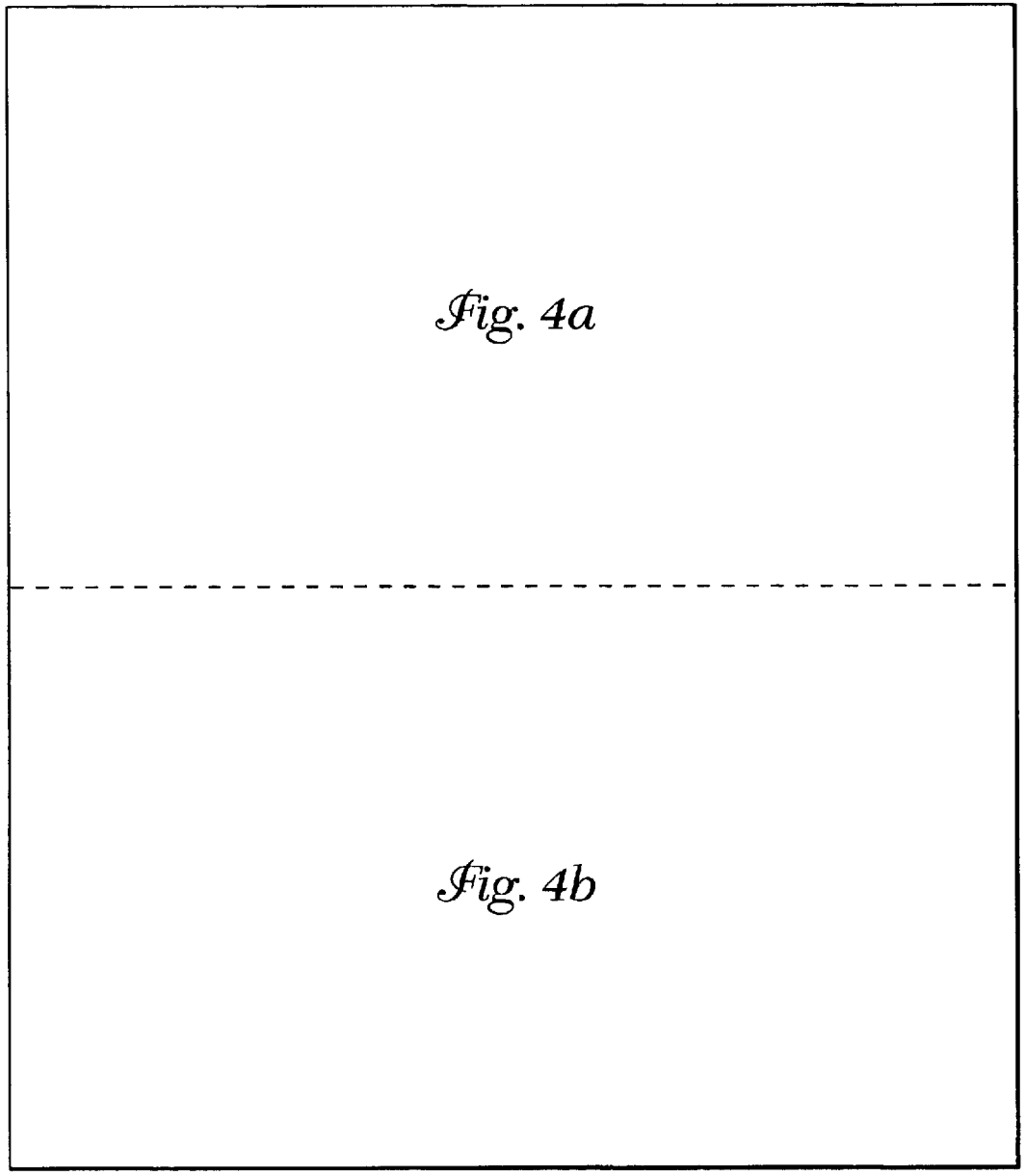
FIG. 4 depicts the coding sequence (SEQ ID NO:1) encoding P. gingivalis DPP-7 (SEQ ID NO:2). Sequences obtained from the Edman degradation of the trypsin fragmented DPP-7 polypeptide chain are underlined. The putative active site serine residue is marked by the black background.

DPP-7 Sequence Analysis—Purified DPP-7 was resolved on SDS-PAGE and electroblotted onto a PVDF membrane. It had an amino-terminal sequence ADKGMMWLLNELN-QENLDRMRELGFT (SEQ ID NO:18). After proteolytic in-gel digestion of the enzyme additional internal sequences were obtained, including: DNKPYK (SEQ ID NO:19), EMTYL (SEQ ID NO:20), FAQFAN (SEQ ID NO:21), VLPAML (SEQ ID NO:22), SVVPY (SEQ ID NO:23), LFFAGL (SEQ ID NO:24). All of this sequence data allowed us to identify the *P. gingivalis* genomic contig gln | TIGR | *P. gingivalis*_ in the Unfinished Microbial Genomes database, TIGR. An ORF corresponding to the DPP-7 amino acid sequence (SEQ ID NO:1) was found, as indicated by the fact, that all sequences of the DPP-7 derived peptides obtained by the enzyme polypeptide fragmentation by trypsin were present in the protein primary structure inferred from the nucleotide sequence of the ORF as shown in FIG. 4. Including a signal peptide (residues 1–24), the entire ORF corresponds to a 712 amino acid polypeptide (see FIG. 4). Interestingly, the DPP-7 ORF contains the consensus sequence for the active-site serine residue of serine type proteases, TGGNSGSPVF (SEQ ID NO:25). As indicated in FIG. 5 the DPP-7 carboxy-terminus (SEQ ID NO:3) exhibits high degree of identity to that of the V8 serine protease (SEQ ID NO:4), particularly around the putative active site serine residue. This is surprising since the *P. gingivalis* DPP-7 is a dipeptidylpeptidase specific for substrates having an aliphatic or an aromatic residue as a substituent on the α-carbon atom of the second amino acid from the N-terminal end of the substrate, whereas *Staphyloccocus aureus* V8 endopeptidase is specific towards substrates including glutamic acid or aspartic acid as the second amino acid from the N-terminal end of the substrate. The similarity search performed using the NCBI TBLASTN tool against GenBank, EMBL, DDBJ and PDB databases showed no significant similarity of DPP-7 to any other known dipeptidylpeptidases, indicating that this enzyme could be regarded as a member of a new family of proteases. Additional searches against databases containing unfinished and finished microbial genomes allowed us to identify more coding sequences encoding similar proteases with consensus active site sequence TGGNSGSPV (FIG. 6; SEQ ID NO:26). A coding sequence of related protein has been found in *P. gingivalis* W83 unfinished portion of complete genome between positions 1360759 and 1362718. This putative proteinase reveals significant similarity to DPP-7 (267/691 identities). Another organism *Shewanella putrefaciens* possesses two related coding sequences (gnl |TIGR_ 24 | sputre 6401 and gnl |TIGR 24 | sputre 6410) while a plant pathogen *Xylella fastidiosa* contains one coding sequence encoding similar proteinase (gb |AE004008.1|). In addition, the computer assisted search for sequential motifs characteristic for transmembrane domains revealed the presence of two such putative regions within the amino-terminal sequence of DPP-7, with residues 7 to 24 and 62 to 78 most likely folded into hydrophobic α-helices responsible for membrane anchoring of this enzyme.

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

| SEQUENCE LISTING FREE TEXT | |
|---|---|
| SEQ ID NO:1 | Coding sequence encoding *Porphyromonas gingivalis* DPP-7 |
| SEQ ID NO:2 | *Porphyromonas gingivalis* DPP-7 |
| SEQ ID NO:3 | C-terminal region of *Porphyromonas gingivalis* DPP-7 |
| SEQ ID NO:4 | C-terminal region of *Staphylococcus aureus* V8 endopeptidase |
| SEQ ID NO:5 | Coding sequence for *Shewanella putrefaciens* gnl |TIGR_24|sputre 6401 |
| SEQ ID NO:6 | Coding sequence for *Shewanella putrefaciens* gnl |TIGR_24|sputre 6410 |
| SEQ ID NO:7 | Coding sequence for *Xylella fastidiosa* gb |AE004008.1| |
| SEQ ID NO:8 | Coding sequence for *Porphyromonas gingivalis* gnl |TIGR|*P. gingivalis*_CPG.con |
| SEQ ID NO:9 | Coding sequence for *Porphyromonas gingivalis* DPP-7 gnl |TIGR|*P. gingivalis*_CPG.con |
| SEQ ID NO:10–17 | Synthetic peptides |
| SEQ ID NO:18 | N-terminal region of *Porphyromonas gingivalis* DPP-7 |
| SEQ ID NO:19–24 | Internal sequences of *Porphyromonas gingivalis* DPP-7 |
| SEQ ID NO:25–26 | Consensus sequences for active sites for serine type proteases |

What is claimed is:

1. An isolated nucleic acid, the complement of which hybridizes to SEQ ID NO: 1 under hybridization conditions of 0.5 M phosohate buffer, pH 7.2, 7% SDS, 10 mM EDTA, at 68° C. followed by three washes for 20 minutes each in 2×SSC, and 0.1% SDS, at 65° C.;

wherein the isolated nucleic acid encodes a protein having dipeptidylpeptidase amidolytic activity;

wherein the isolated nucleic acid has a nucleotide sequence comprising SEQ ID NO: 1; and wherein the dipeptidylpeptidase amidolytic activity is defined as activity for cleaving the peptide bond between the second and the third amino acids from the unblocked amino-terminal end of a target polypeptide having an aliphatic or an aromatic residue as asubstituent on the α-carbon atom of the second amino acid from the unblocked amino-terminal end of the polpeptide, with the proviso that the second amino acid from the unblocked amino-terminal end of the polypeptide is not charged.

2. An isolated nucleic acid comprising a nucleotide sequence having at least about 95% identity with SEQ ID NO: 1;

wherein the nucleotide sequence encodes a protein having dipeptidylpeptidase amidolytic activity; and wherein the dipeptidylpeptidase amidolytic activity is defined as activity for cleaving the peptide bond between the second and the third amino acids from the unblocked amino-terminal end of a tareet polypeotide having an aliphatic or an aromatic residue as a substituent on the α-carbon atom of the second amino acid from thc unblocked amino-terminal end of the polypeinide, with the proviso that the second amino acid from the unblocked amino-terminal end of the polypeptide is not charged.

3. An isolated nucleic acid consisting of nucleotide sequence SEQ ID NO: 1.

* * * * *

UNITED STATES PATENT AND TRADEMARK OFFICE
CERTIFICATE OF CORRECTION

PATENT NO. : 6,864,363 B2
DATED : March 8, 2005
INVENTOR(S) : Travis et al.

It is certified that error appears in the above-identified patent and that said Letters Patent is hereby corrected as shown below:

Column 5,
Line 13, delete "(▼)" and insert -- (▲) --

Column 51,
Lines 28 and 29, delete "asubstituent" and insert -- a substituent --

Column 52,
Lines 23, delete "tareet polypeotide" and insert -- target polypeptide --
Line 27, delete "polypeinide" and insert -- polypeptide --

Signed and Sealed this

Thirty-first Day of May, 2005

JON W. DUDAS
*Director of the United States Patent and Trademark Office*

SEQUENCE LISTING

<160> NUMBER OF SEQ ID NOS: 26

<210> SEQ ID NO 1
<211> LENGTH: 2139
<212> TYPE: DNA
<213> ORGANISM: Porphyromonas gingivalis

<400> SEQUENCE: 1

```
atgcaaatga aattaaaaag tattcttctc ggagcagccc tgctgttggg tgcttcaggg      60
gtagccaaag ccgacaaagg catgtggctc ctcaacgaac tcaatcagga gaatctggat     120
cgaatgcgtg agctcggctt tacgctcccg ttggattcgc tctacagttt cgacaagccg     180
tccattgcca atgccgtggt tatcttcggt ggcggatgta ccggtatcac agtgtccgat     240
cagggcctga tctttaccaa ccaccactgc ggatacggtg ctatccagag ccaaagcacg     300
gtggatcacg actatctgcg cgatggtttc gtttctcgca cgatgggtga ggagcttccg     360
attccgggtc tttccgtgaa gtatctgcgc aagatcgtga aggtaacgga caaggtagaa     420
ggacagctca aggtatcac tgacgagatg gagcgtctgc gcaaagctca ggaggtatgc     480
caagaactgg ccaaaaaaga aaatgcagac gagaaccaac tctgcatcgt agagcctttc     540
tattccaaca cgaatactt cctcatcgtc tacgatgtat tcaaggacgt tcgtatggta     600
tttgctcctc ccagctctgt aggtaagttc ggaggcgata cggacaactg gatgtggccg     660
cgtcacacgg gcgacttcag cgtattccgc gtgtatgccg gtgccgacaa ccggccggcc     720
gaatacagca aggacaataa accctataag cccgtttact tcgctgccgt atccatgcaa     780
ggctacaagg ctgacgacta tgccatgacc atcggttttcc cgggcagtac ggatcgctac     840
ctcacttctt ggggtgtgga agatcgtatc gaaaacgaga caatcctcg tatcgaagtt     900 cgcggtatca gcaaggcat ctggaaggaa gccatgagcg cagatcaggc tacccgtatc     960
aaatatgcca gcaagtatgc tcagagtgct aactattgga agaattcgat cggtatgaac    1020
cgcggtctcg ctcgtcttga cgtgataggt cgtaagcgtg ccgaggaaag agcattcgca    1080
gactggatcc gtaagaacgg caagagtgct gtctatggcg atgtattgtc ttctctcgaa    1140
aaggcttata ggaaggagc caaggccaac cgtgagatga cttatttgag cgagacgctc    1200
ttcggtggta ccgaggtggt tcgttttgca cagtttgcca acgcattggc tacaaatcct    1260
gatgctcatg ccgtatcct caaatcgctt gacgacaagt acaaagacta cctcccctcg    1320
ctcgaccgta aggtgctgcc cgccatgctc gatattgtac gccggcgtat ccctgccgac    1380
aagctccccg atatattcaa gaatgtaatc gacaagaaat tcaaggcga cacgaagaag    1440 tatgcagact tcgtattcga caagagtgtg gttccttata gcgacaagtt ccatgccatg    1500
ctcaagtcca tggacaagga aaagtttgcc aaggctatcg agaaagatcc ggcagtagag    1560
ctttccaaga gcgtaatagc tgctgctcgc gctattcagg ccgatgcgat ggccaatgcc    1620
tatgccattg agaagggcaa gcgtctttc tttgccggtt tgcgtgagat gtaccccgga    1680
cgtgctctgc cgagcgatgc caacttcacc atgcgtatga gctacggctc catcaaggga    1740
tatgaaccgc aggacggtgc ctggtacaac tatcatacga caggcaaggg cgtattggag    1800
aagcaggatc ctaagagcga tgagtttgcc gtacaggaga atatcctcga cctcttccgc    1860
accaaaaact atggtcgcta tgccgagaac ggtcagctcc atatcgcttt cctatcgaac    1920
aacgacatca cggcggtaa ctccggtagc ccgtattcg ataagaacgg ccgtctgatc    1980
ggtcttgctt tcgatggcaa ctgggaagct atgagtggtg acatcgagtt cgaacccgat    2040
```

```
ctgcagcgca caatcagcgt ggacatccgc tacgttctct tcatgattga caaatggggt      2100
cagtgccccc gtctcatcca agagctgaag ttgatctaa                             2139
```

<210> SEQ ID NO 2
<211> LENGTH: 712
<212> TYPE: PRT
<213> ORGANISM: Porphyromonas gingivalis

<400> SEQUENCE: 2

```
Met Gln Met Lys Leu Lys Ser Ile Leu Leu Gly Ala Ala Leu Leu Leu
1               5                   10                  15

Gly Ala Ser Gly Val Ala Lys Ala Asp Lys Gly Met Trp Leu Leu Asn
                20                  25                  30

Glu Leu Asn Gln Glu Asn Leu Asp Arg Met Arg Glu Leu Gly Phe Thr
            35                  40                  45

Leu Pro Leu Asp Ser Leu Tyr Ser Phe Asp Lys Pro Ser Ile Ala Asn
        50                  55                  60

Ala Val Val Ile Phe Gly Gly Cys Thr Gly Ile Thr Val Ser Asp
65                  70                  75                  80

Gln Gly Leu Ile Phe Thr Asn His His Cys Gly Tyr Gly Ala Ile Gln
                85                  90                  95

Ser Gln Ser Thr Val Asp His Asp Tyr Leu Arg Asp Gly Phe Val Ser
            100                 105                 110

Arg Thr Met Gly Glu Glu Leu Pro Ile Pro Gly Leu Ser Val Lys Tyr
        115                 120                 125

Leu Arg Lys Ile Val Lys Val Thr Asp Lys Val Glu Gly Gln Leu Lys
    130                 135                 140

Gly Ile Thr Asp Glu Met Glu Arg Leu Arg Lys Ala Gln Glu Val Cys
145                 150                 155                 160

Gln Glu Leu Ala Lys Lys Glu Asn Ala Asp Glu Asn Gln Leu Cys Ile
                165                 170                 175

Val Glu Pro Phe Tyr Ser Asn Asn Glu Tyr Phe Leu Ile Val Tyr Asp
            180                 185                 190

Val Phe Lys Asp Val Arg Met Val Phe Ala Pro Pro Ser Ser Val Gly
        195                 200                 205

Lys Phe Gly Gly Asp Thr Asp Asn Trp Met Trp Pro Arg His Thr Gly
    210                 215                 220

Asp Phe Ser Val Phe Arg Val Tyr Ala Gly Ala Asp Asn Arg Pro Ala
225                 230                 235                 240

Glu Tyr Ser Lys Asp Asn Lys Pro Tyr Lys Pro Val Tyr Phe Ala Ala
                245                 250                 255

Val Ser Met Gln Gly Tyr Lys Ala Asp Asp Tyr Ala Met Thr Ile Gly
            260                 265                 270

Phe Pro Gly Ser Thr Asp Arg Tyr Leu Thr Ser Trp Gly Val Glu Asp
        275                 280                 285

Arg Ile Glu Asn Glu Asn Asn Pro Arg Ile Glu Val Arg Gly Ile Lys
    290                 295                 300

Gln Gly Ile Trp Lys Glu Ala Met Ser Ala Asp Gln Ala Thr Arg Ile
305                 310                 315                 320

Lys Tyr Ala Ser Lys Tyr Ala Gln Ser Ala Asn Tyr Trp Lys Asn Ser
                325                 330                 335

Ile Gly Met Asn Arg Gly Leu Ala Arg Leu Asp Val Ile Gly Arg Lys
            340                 345                 350
```

```
Arg Ala Glu Glu Arg Ala Phe Ala Asp Trp Ile Arg Lys Asn Gly Lys
            355                 360                 365

Ser Ala Val Tyr Gly Asp Val Leu Ser Ser Leu Glu Lys Ala Tyr Lys
        370                 375                 380

Glu Gly Ala Lys Ala Asn Arg Glu Met Thr Tyr Leu Ser Glu Thr Leu
385                 390                 395                 400

Phe Gly Gly Thr Glu Val Val Arg Phe Ala Gln Phe Ala Asn Ala Leu
                405                 410                 415

Ala Thr Asn Pro Asp Ala His Ala Gly Ile Leu Lys Ser Leu Asp Asp
            420                 425                 430

Lys Tyr Lys Asp Tyr Leu Pro Ser Leu Asp Arg Lys Val Leu Pro Ala
        435                 440                 445

Met Leu Asp Ile Val Arg Arg Ile Pro Ala Asp Lys Leu Pro Asp
450                 455                 460

Ile Phe Lys Asn Val Ile Asp Lys Lys Phe Lys Gly Asp Thr Lys Lys
465                 470                 475                 480

Tyr Ala Asp Phe Val Phe Asp Lys Ser Val Val Pro Tyr Ser Asp Lys
                485                 490                 495

Phe His Ala Met Leu Lys Ser Met Asp Lys Glu Lys Phe Ala Lys Ala
            500                 505                 510

Ile Glu Lys Asp Pro Ala Val Glu Leu Ser Lys Ser Val Ile Ala Ala
        515                 520                 525

Ala Arg Ala Ile Gln Ala Asp Ala Met Ala Asn Ala Tyr Ala Ile Glu
    530                 535                 540

Lys Gly Lys Arg Leu Phe Phe Ala Gly Leu Arg Glu Met Tyr Pro Gly
545                 550                 555                 560

Arg Ala Leu Pro Ser Asp Ala Asn Phe Thr Met Arg Met Ser Tyr Gly
                565                 570                 575

Ser Ile Lys Gly Tyr Glu Pro Gln Asp Gly Ala Trp Tyr Asn Tyr His
            580                 585                 590

Thr Thr Gly Lys Gly Val Leu Glu Lys Gln Asp Pro Lys Ser Asp Glu
        595                 600                 605

Phe Ala Val Gln Glu Asn Ile Leu Asp Leu Phe Arg Thr Lys Asn Tyr
    610                 615                 620

Gly Arg Tyr Ala Glu Asn Gly Gln Leu His Ile Ala Phe Leu Ser Asn
625                 630                 635                 640

Asn Asp Ile Thr Gly Asn Ser Gly Ser Pro Val Phe Asp Lys Asn
                645                 650                 655

Gly Arg Leu Ile Gly Leu Ala Phe Asp Gly Asn Trp Glu Ala Met Ser
            660                 665                 670

Gly Asp Ile Glu Phe Glu Pro Asp Leu Gln Arg Thr Ile Ser Val Asp
        675                 680                 685

Ile Arg Tyr Val Leu Phe Met Ile Asp Lys Trp Gly Gln Cys Pro Arg
    690                 695                 700

Leu Ile Gln Glu Leu Lys Leu Ile
705                 710

<210> SEQ ID NO 3
<211> LENGTH: 52
<212> TYPE: PRT
<213> ORGANISM: Porphyromonas gingivalis

<400> SEQUENCE: 3

Thr Gly Gly Asn Ser Gly Ser Pro Val Phe Asp Lys Asn Gly Arg Leu
1               5                   10                  15
```

```
Ile Gly Leu Ala Phe Asp Gly Asn Trp Glu Ala Met Ser Gly Asp Ile
            20                  25                  30

Glu Phe Glu Pro Asp Leu Gln Arg Thr Ile Ser Val Asp Ile Arg Tyr
            35                  40                  45

Val Leu Phe Met
     50

<210> SEQ ID NO 4
<211> LENGTH: 52
<212> TYPE: PRT
<213> ORGANISM: Staphylococcus aureus

<400> SEQUENCE: 4

Thr Gly Gly Asn Ser Gly Ser Pro Val Phe Asn Glu Lys Asn Glu Val
1               5                   10                  15

Ile Gly Ile His Trp Gly Gly Val Pro Asn Glu Phe Asn Gly Ala Val
            20                  25                  30

Phe Ile Asn Glu Asn Val Arg Asn Phe Leu Lys Gln Asn Ile Glu Asp
            35                  40                  45

Ile His Phe Ala
     50

<210> SEQ ID NO 5
<211> LENGTH: 734
<212> TYPE: PRT
<213> ORGANISM: Shewanella putrefaciens

<400> SEQUENCE: 5

Met Ala Ser Gln Ala Leu Gly Phe Leu His Gln Asn Gly Leu Asn Thr
1               5                   10                  15

Met Lys Lys Trp Leu Leu Ser Val Ala Val Ala Ala Ser Phe Ala Ser
            20                  25                  30

His Ala Asp Glu Gly Met Trp Gln Pro His Gln Leu Pro Ala Met Ala
            35                  40                  45

Asp Val Leu Lys Ala Lys Gly Leu Glu Ile Asp Ala Lys Ser Ile Ser
        50                  55                  60

Lys Leu Thr Glu Phe Pro Met Asn Ala Val Ile Ser Leu Gly Gly Cys
65                  70                  75                  80

Thr Ala Ser Phe Val Ser Pro Lys Gly Leu Val Thr Asn His His
                85                  90                  95

Cys Ala Tyr Gly Ser Ile Gln Tyr Asn Ser Thr Pro Glu Lys Asn Leu
            100                 105                 110

Leu Gln Asp Gly Phe Leu Ala Lys Thr Phe Ala Asp Glu Leu Pro Ala
            115                 120                 125

Ala Pro Gly Ser Arg Val Tyr Val Thr Glu Asp Val Thr Asn Val Thr
        130                 135                 140

Glu Arg Val Lys Ala Gly Leu Glu Asn Lys Thr Gly Arg Glu Phe Tyr
145                 150                 155                 160

Gln Gly Val Glu Asn Gln Glu Lys Ala Leu Val Ala Glu Cys Glu Lys
                165                 170                 175

Asp Glu Gly Tyr Arg Cys Gln Val Tyr Ser Phe His Gly Gly Leu Glu
            180                 185                 190

Tyr Tyr Leu Val Lys Gln Leu Glu Ile Arg Asp Val Arg Leu Val Tyr
            195                 200                 205

Asn Pro Ala Gly Ser Val Gly Lys Tyr Gly Gly Asp Val Asp Asn Trp
        210                 215                 220
```

```
Met Trp Pro Arg His Thr Gly Asp Tyr Ser Phe Tyr Arg Ala Tyr Val
225                 230                 235                 240

Ser Lys Asn Gly Lys Pro Ala Glu Phe Ser Ala Asp Asn Val Pro Tyr
            245                 250                 255

Glu Pro Lys Ser Phe Leu Lys Val Ser Ala Lys Gly Val Ser Glu Gly
            260                 265                 270

Asp Phe Val Met Val Ala Gly Tyr Pro Gly Arg Thr Asn Arg Tyr Arg
            275                 280                 285

Thr Ala Thr Glu Val Gln Asn Glu Phe Glu Trp Ala Tyr Pro Glu Gly
            290                 295                 300

Lys Met Leu Arg Glu Arg Phe Ile Glu Ile Ile Lys Ala Thr Ala Pro
305                 310                 315                 320

Glu Gly Ser Asp Glu Arg Ile Lys Tyr Glu Ser Gln Ile Ala Gly Leu
            325                 330                 335

Ala Asn Tyr Ala Lys Asn Phe Thr Ser Met Ile Glu Phe Tyr Gly Lys
            340                 345                 350

Ser Thr Met Leu Ala Asp Arg Lys Ala Leu Glu Ala Lys Leu Ala Glu
            355                 360                 365

Trp Ile Ala Lys Asp Ser Ser Arg Glu Ala Lys Tyr Gly Lys Thr Leu
370                 375                 380

Ala Glu Leu Asp Ala Leu Ile Ala Lys Ser Lys Ala His Gln Glu Arg
385                 390                 395                 400

Asp Met Ile Leu Ser Tyr Ile Ser Ser Thr Thr Met Leu Pro Thr Ala
            405                 410                 415

Asn Asn Leu Tyr Arg Leu Ala His Glu Lys Gln Leu Pro Asp Met Gln
            420                 425                 430

Arg Glu Pro Gly Phe Gln Asp Arg Asp Met Thr Arg Phe Lys Ala Ser
            435                 440                 445

Met Glu Arg Ile Asp Arg Arg Tyr Ala Ala Ser Val Asp Lys Ala Val
            450                 455                 460

Leu Phe Asp Met Leu Lys Arg Tyr Ala Ala Leu Pro Glu Ala Gln Arg
465                 470                 475                 480

Leu Pro Ala Met Asp Lys Ala Phe Gly Ile Asp Asn Lys Val Asn Glu
            485                 490                 495

Ala Lys Leu Ala Lys Thr Leu Asp Lys Met Tyr Ala Lys Thr Glu Leu
            500                 505                 510

Gly Asn Lys Asp Val Arg Leu Ala Trp Met Glu Lys Ser Val Asp Asp
            515                 520                 525

Phe Lys Ala Ser Lys Asp Pro Phe Ile Gln Phe Ala Val Ala Met Tyr
530                 535                 540

Asp Thr Asn Met Ser Glu Glu Lys Lys Glu Lys Glu Leu Asp Gly Glu
545                 550                 555                 560

Leu Met Lys Val Arg Pro Gln Tyr Met Asp Ala Ile Ile Ala Tyr Asn
            565                 570                 575

Leu Glu Gln Gly Lys Pro Val Tyr Ala Asp Ala Asn Ser Ser Leu Arg
            580                 585                 590

Val Thr Val Gly His Val Lys Gly Tyr Ser Pro Lys Asp Gly Leu Val
            595                 600                 605

Ala Val Pro Phe Thr Arg Leu Glu Gly Ile Val Gln Lys Asp Thr Gly
            610                 615                 620

Ile Asp Pro Phe Asp Ala Pro Lys Gln Gln Leu Glu Leu Ile Lys Gln
625                 630                 635                 640
```

-continued

Lys Gln Tyr Gly Asp Phe Tyr Met Lys Ser Ile Asp Ser Val Pro Val
            645                 650                 655

Asn Phe Leu Ser Thr Leu Asp Thr Thr Gly Asn Ser Gly Ser Pro
            660                 665                 670

Thr Leu Asn Gly Arg Ala Glu Leu Val Gly Leu Leu Phe Asp Gly Val
            675                 680                 685

Tyr Glu Ser Ile Ile Gly Gly Trp Ala Phe Asp Asn Glu Ile Asn Arg
            690                 695                 700

Ser Ile His Val Asp Ser Arg Tyr Met Leu Trp Val Met Lys Tyr Leu
705                 710                 715                 720

Asp His Ala Asp Asn Leu Leu Ala Glu Met Glu Ile Val Asn
            725                 730

<210> SEQ ID NO 6
<211> LENGTH: 732
<212> TYPE: PRT
<213> ORGANISM: Shewanella putrefaciens

<400> SEQUENCE: 6

Met Arg Ile Ala Leu Val Ala Ala Leu Val Leu Thr Cys Gly Ile Ala
1               5                   10                  15

Thr Ala Asp Glu Gly Gln Trp Gln Pro Tyr Gln Met Pro Ser Ile Ala
            20                  25                  30

Asp Lys Leu Ser Ala Arg Gly Ile Asp Ile Pro Ala Asp Lys Leu Ala
            35                  40                  45

Asp Leu Thr Ser Tyr Pro Met Asn Ala Val Gly Leu Gly Tyr Cys
    50                  55                  60

Thr Ala Ser Phe Val Ser Pro Gln Gly Leu Val Val Thr Asn His His
65                  70                  75                  80

Cys Ala Tyr Lys Ala Ile Gln Tyr Asn Thr Lys Lys Glu His Asn Tyr
                85                  90                  95

Leu Glu Gln Gly Phe Leu Ala Thr Ser Met Asp Lys Glu Pro Ser Ala
            100                 105                 110

Gly Pro Asn Glu Arg Leu Tyr Ile Thr Glu Ala Val Thr Asp Val Thr
            115                 120                 125

Ser Asp Val Thr Lys Asp Leu Ser Gln Asp Pro Leu Lys Arg Tyr Glu
    130                 135                 140

Glu Ile Glu Asn His Ser Lys Ala Leu Ile Lys Ser Cys Glu Ala Asp
145                 150                 155                 160

Asp Asn Tyr Arg Cys Asn Val Arg Ser Phe His Asn Gly Leu Glu Tyr
                165                 170                 175

Tyr Leu Ile Lys Gln Leu Met Ile Arg Asp Val Arg Leu Val Tyr Ala
            180                 185                 190

Pro Pro Glu Ser Val Gly Gly Tyr Gly Gly Asp Ile Asp Asn Tyr Glu
            195                 200                 205

Tyr Pro Arg His Ser Gly Asp Phe Ala Phe Leu Arg Ala Tyr Val Gly
            210                 215                 220

Lys Asp Gly Lys Pro Ala Ala Phe Ser Glu Asp Asn Ile Pro Tyr Thr
225                 230                 235                 240

Pro Lys Ser Tyr Leu Lys Val Asn Ala Asp Gly Val Lys Ala Gly Asp
                245                 250                 255

Gly Val Phe Val Ala Gly Tyr Pro Gly Thr Thr Asn Arg Tyr Asn Leu
            260                 265                 270

Thr Ser Glu Leu Lys Phe Ala Ser Asp Trp Leu Tyr Pro Thr Gln Ala
            275                 280                 285

-continued

```
Lys Arg Tyr Gln Leu Gln Ile Asp Thr Ile Glu Ala Met Gly Gln Lys
    290                 295                 300
Asp Ala Asp Ile Ala Ile Lys Tyr Ala Gly Asn Met Ala Ser Met Ala
305                 310                 315                 320
Asn Arg Met Lys Lys Leu Asn Gly Leu Leu Ala Gly Phe Lys Ala Thr
                325                 330                 335
Asp Ile Val Gly Ile Lys Gln Gln Arg Glu Asn Asp Phe Leu Ala Trp
            340                 345                 350
Leu Thr Lys Asn Pro Asn Leu Asn Gln Asn Leu Ile Ser Glu Leu Glu
        355                 360                 365
Val Leu Leu Ala Glu Gln Gln Leu Gln Thr Gln Thr Asn Tyr Tyr Phe
    370                 375                 380
Thr Asn Ala Gln Ser Ser Thr Leu Leu Thr Ala Ala Asn Asn Leu Tyr
385                 390                 395                 400
Arg Leu Ala Lys Glu Lys Gln Lys Ser Asp Ala Glu Arg Glu Ile Gly
                405                 410                 415
Tyr Gln Glu Arg Asp Leu Ala Met Phe Ser Ser Arg Leu Lys Arg Ile
            420                 425                 430
Asp Ser Ser Phe Asp Val Lys Val Asp Lys Thr Leu Trp Leu Gln Asp
        435                 440                 445
Leu Asn Ala Tyr Leu Ser Gln Pro Asn Arg Val Ala Ala Leu Asp Asn
    450                 455                 460
Met Leu Asn Leu Asn Asp Lys Asn Val Ser Leu Ala Ala Lys Leu Asp
465                 470                 475                 480
Gly Leu Tyr Ser Leu Thr Thr Leu Thr Asp Gln Ala Gln Arg Leu Ala
                485                 490                 495
Trp Met Glu Ala Asp Ala Lys Ala Phe Glu Thr Ser Ser Asp Pro Phe
            500                 505                 510
Ile Arg Leu Ala Val Ala Leu Tyr Asp Thr Asn Met Ala Gln Glu Lys
        515                 520                 525
Ala Glu Lys Ile Leu Ala Gly Lys Leu Ser Thr Ala Arg Pro Ala Tyr
    530                 535                 540
Met Ala Ala Val Ile Asp Tyr Tyr Lys Ala Asn Asn Trp Pro Val Tyr
545                 550                 555                 560
Pro Asp Ala Asn Gly Thr Leu Arg Ile Ser Tyr Gly Met Val Asp Gly
                565                 570                 575
Tyr Gln Ser Arg Asp Ala Leu Tyr Lys Gln Pro Phe Thr Arg Leu Asp
            580                 585                 590
Gly Ile Val Ala Lys His Thr Gly Val Glu Pro Tyr Asn Ala Pro Lys
        595                 600                 605
Lys Leu Leu Asp Ala Ile Ser Val Gln Arg Phe Gly Asp His Leu Val
    610                 615                 620
Lys Ser Val Tyr Gln Asp Pro Arg Gly Trp Ile Cys Arg Leu Phe Ser
625                 630                 635                 640
Cys Leu Asp Lys Pro Glu Glu Phe Asn Ser Val Pro Val Asn Phe Leu
                645                 650                 655
Ser Ser Val Asp Thr Thr Gly Gly Asn Ser Gly Ser Pro Val Phe Asn
            660                 665                 670
Gly Lys Gly Glu Leu Val Gly Leu Asn Phe Asp Ser Thr Tyr Glu Ala
        675                 680                 685
Ile Thr Lys Asp Trp Phe Phe Asn Pro Thr Ile Thr Arg Ala Val His
    690                 695                 700
```

-continued

Val Asp Ile Arg Tyr Ile Leu Trp Met Met Asp Glu Val Asp His Ala
705                 710                 715                 720

Asp Asn Leu Ile Lys Glu Leu Asp Leu Val Arg Asn
            725                 730

<210> SEQ ID NO 7
<211> LENGTH: 716
<212> TYPE: PRT
<213> ORGANISM: Xylella fastidiosa

<400> SEQUENCE: 7

Met Arg Phe Asn Leu Leu Ser Leu Ser Val Leu Ala Thr Leu Ile Thr
1               5                   10                  15

Val Asp Ser Thr His Ala Gly Glu Gly Met Trp Val Pro Gln Gln Leu
            20                  25                  30

Pro Glu Ile Ala Gly Pro Leu Lys Gln Ala Gly Leu Gln Leu Ser Pro
            35                  40                  45

Glu Gln Leu Ser Asn Leu Thr Gly Asp Pro Met Gly Ala Val Val Ser
    50                  55                  60

Leu Gly Asn Cys Thr Ala Ser Leu Val Ser Pro Glu Gly Leu Val Ile
65              70                  75                  80

Thr Asn His His Cys Ala Tyr Gly Ala Ile Gln Leu Asn Ser Thr Pro
                85                  90                  95

Lys Lys Asn Leu Ile Lys Glu Gly Phe Asn Ala Leu Thr Gln Ala Asp
            100                 105                 110

Glu Val Ser Ala Gly Pro Asn Ala Arg Ile Tyr Val Leu Glu Gln Ile
        115                 120                 125

Thr Asp Val Thr Ala Gln Ala Lys Ala Ala Leu Ala Ala Ala Gly Asn
    130                 135                 140

Asp Pro Phe Lys Arg Thr Thr Ala Leu Glu Thr Phe Ser Lys Gln Glu
145                 150                 155                 160

Ile Ala Lys Cys Glu Glu Glu Gln Gly Tyr Arg Cys Gln Phe Phe Ser
                165                 170                 175

Phe Ala Gly Gly Asn Thr Tyr Arg Val Phe Lys Asn Leu Glu Ile Lys
            180                 185                 190

Asp Val Arg Leu Val Tyr Ala Pro Gln Gly Ser Val Gly Lys Phe Gly
        195                 200                 205

Gly Asp Val Asp Asn Trp Met Trp Pro Arg His Thr Gly Asp Phe Ser
    210                 215                 220

Phe Tyr Arg Ala Tyr Val Gly Lys Asp Gly Lys Pro Ala Ser Phe Ser
225                 230                 235                 240

Lys Glu Asn Ile Pro Tyr Arg Pro Lys His Trp Leu Lys Phe Ser Asp
                245                 250                 255

Gln Pro Leu Gly Asp Gly Asp Phe Val Met Val Ala Gly Tyr Pro Gly
            260                 265                 270

Arg Thr Asn Arg Tyr Ala Leu Val Ala Glu Phe Glu Asn Thr Ala His
        275                 280                 285

Trp Thr Tyr Pro Val Ile Gly Gln His Phe Lys Asn Leu Ile Ala Leu
    290                 295                 300

Ile Glu Ala Ala Ser Lys Gln Asn Pro Asp Ile Gln Val Lys Tyr Ala
305                 310                 315                 320

Ser Thr Leu Ala Gly Leu Asn Asn Thr Ser Lys Asn Phe Asp Gly Gln
                325                 330                 335

Leu Asp Gly Phe Arg Arg Ile Asn Ala Ile Gly Gln Lys Gln Ser Glu
            340                 345                 350

-continued

```
Glu Thr Ala Val Leu Ala Trp Leu Lys Gln Gln Gly Ile Arg Gly His
            355                 360                 365
Glu Ala Leu Ala Ala His Gln Thr Leu Val Asp Leu Thr Glu Gln Tyr
        370                 375                 380
Lys Ala Asn Gln Asp Arg Asp Phe Val Leu Gly Gln Phe Asn Gly Ser
385                 390                 395                 400
Gly Val Ile Gly Val Ala Val Asn Leu Tyr Arg Leu Ala Ile Glu Arg
                405                 410                 415
Thr Lys Ser Asp Ala Gln Arg Glu Ala Gly Tyr Gln Glu Arg Asp Leu
            420                 425                 430
Pro Thr Ile Glu Gly Asn Leu Lys Gln Met Glu Arg Arg Tyr Leu Pro
        435                 440                 445
Glu Met Asp Arg Gln Met Gln Gln Tyr Trp Leu Thr Glu Tyr Asn Lys
    450                 455                 460
Leu Pro Val Lys Gln Arg Val Ala Ala Ile Asp Val Trp Leu Gly Asp
465                 470                 475                 480
Gly Ile Pro Ala Thr Leu Lys Arg Leu Gly Asp Thr Lys Leu Ser Ser
                485                 490                 495
Ser Glu Glu Arg Leu Lys Trp Phe Asn Ala Asp Arg Ala Ala Phe Glu
            500                 505                 510
Ser Ser Gln Asp Pro Ala Ile Arg Tyr Ala Val Ala Ile Met Pro Ala
        515                 520                 525
Leu Leu Glu Ile Glu Arg Gln Asn Lys Ile Arg Thr Gly Glu Leu Leu
    530                 535                 540
Lys Ala Arg Pro Ile Tyr Leu Gln Ala Leu Ala Asp Tyr Asn Lys Ser
545                 550                 555                 560
His Gly Lys Phe Val Tyr Pro Asp Ala Asn Ser Ser Leu Arg Ile Thr
                565                 570                 575
Phe Gly His Val Lys Gly Tyr Ser Pro Lys Asp Gly Val Glu Tyr Thr
            580                 585                 590
Pro Phe Thr Thr Leu Gln Gly Val Met Ala Lys Asn Thr Gly Val Glu
        595                 600                 605
Pro Phe Asp Ser Pro Lys Ser Leu Ile Asn Ala Ile Lys Ala Lys Ser
    610                 615                 620
Tyr Ala Asn Leu Ala Asp Gln Arg Ile Gly Thr Val Pro Val Asn Phe
625                 630                 635                 640
Leu Ser Asp Leu Asp Ile Thr Gly Gly Asn Ser Gly Ser Pro Val Leu
                645                 650                 655
Asp Ala His Gly Lys Leu Val Gly Leu Ala Phe Asp Gly Asn Trp Glu
            660                 665                 670
Ser Val Ser Ser Asn Trp Val Phe Asp Pro Val Met Thr Arg Thr Ile
        675                 680                 685
Ala Val Asp Ser Arg Tyr Val Gln Trp Ile Met Thr Glu Val Ala Pro
    690                 695                 700
Ala Pro His Leu Leu Lys Glu Leu Asn Leu Tyr Arg
705                 710                 715
```

<210> SEQ ID NO 8
<211> LENGTH: 699
<212> TYPE: PRT
<213> ORGANISM: Porphyromonas gingivalis

<400> SEQUENCE: 8

Met Gln Met Lys Leu Lys Ser Ile Leu Leu Gly Ala Ala Leu Leu Leu

-continued

```
1               5                  10                 15
Gly Ala Ser Gly Val Ala Lys Ala Asp Lys Gly Met Trp Leu Leu Asn
                20                  25                 30

Glu Leu Asn Gln Glu Asn Leu Asp Arg Met Arg Glu Leu Gly Phe Thr
                35                  40                 45

Leu Pro Leu Asp Ser Leu Tyr Ser Phe Asp Lys Pro Ser Ile Ala Asn
                50                  55                 60

Ala Val Val Ile Phe Gly Gly Cys Thr Gly Ile Thr Val Ser Asp
65                  70                  75                 80

Gln Gly Leu Ile Phe Thr Asn His His Cys Gly Tyr Gly Ala Ile Gln
                85                  90                 95

Ser Gln Ser Thr Val Asp His Asp Tyr Leu Arg Asp Gly Phe Val Ser
                100                 105                110

Arg Thr Met Gly Glu Glu Leu Pro Ile Pro Gly Leu Ser Val Lys Tyr
                115                 120                125

Leu Arg Lys Ile Val Lys Val Thr Asp Lys Val Glu Gly Gln Leu Lys
                130                 135                140

Gly Ile Thr Asp Glu Met Glu Arg Leu Arg Lys Ala Gln Glu Val Cys
145                 150                 155                160

Gln Glu Leu Ala Lys Lys Glu Asn Ala Asp Glu Asn Gln Leu Cys Ile
                165                 170                175

Val Glu Pro Phe Tyr Ser Asn Asn Glu Tyr Phe Leu Ile Val Tyr Asp
                180                 185                190

Val Phe Lys Asp Val Arg Met Val Phe Ala Pro Pro Ser Ser Val Gly
                195                 200                205

Lys Phe Gly Gly Asp Thr Asp Asn Trp Met Trp Pro Arg His Thr Gly
                210                 215                220

Asp Phe Ser Val Phe Arg Val Tyr Ala Gly Ala Asp Asn Arg Pro Ala
225                 230                 235                240

Glu Tyr Ser Lys Asp Asn Lys Pro Tyr Lys Pro Val Tyr Phe Ala Ala
                245                 250                255

Val Ser Met Gln Gly Tyr Lys Ala Asp Asp Tyr Ala Met Thr Ile Gly
                260                 265                270

Phe Pro Gly Ser Thr Asp Arg Tyr Leu Thr Ser Trp Gly Val Glu Asp
                275                 280                285

Arg Ile Glu Asn Glu Asn Asn Pro Arg Ile Glu Val Arg Gly Ile Lys
                290                 295                300

Gln Gly Ile Trp Lys Glu Ala Met Ser Ala Asp Gln Ala Thr Arg Ile
305                 310                 315                320

Lys Tyr Ala Ser Lys Tyr Ala Gln Ser Ala Asn Tyr Trp Lys Asn Ser
                325                 330                335

Ile Gly Met Asn Arg Gly Leu Ala Arg Leu Asp Val Ile Gly Arg Lys
                340                 345                350

Arg Ala Glu Glu Arg Ala Phe Ala Asp Trp Ile Arg Lys Asn Gly Lys
                355                 360                365

Ser Ala Val Tyr Gly Asp Val Leu Ser Ser Leu Glu Lys Ala Tyr Lys
                370                 375                380

Glu Gly Ala Lys Ala Asn Arg Glu Met Thr Tyr Leu Ser Glu Thr Leu
385                 390                 395                400

Phe Gly Gly Thr Glu Val Val Arg Phe Ala Gln Phe Ala Asn Ala Leu
                405                 410                415

Ala Thr Asn Pro Asp Ala His Ala Gly Ile Leu Lys Ser Leu Asp Asp
                420                 425                430
```

-continued

```
Lys Tyr Lys Asp Tyr Leu Pro Ser Leu Asp Arg Lys Val Leu Pro Ala
            435                 440                 445

Met Leu Asp Ile Val Arg Arg Ile Pro Ala Asp Lys Leu Pro Asp
    450                 455                 460

Ile Phe Lys Asn Val Ile Asp Lys Lys Phe Lys Gly Asp Thr Lys Lys
465                 470                 475                 480

Tyr Ala Asp Phe Val Phe Asp Lys Ser Val Val Pro Tyr Ser Asp Lys
                485                 490                 495

Phe His Ala Met Leu Lys Ser Met Asp Lys Glu Lys Phe Ala Lys Ala
                500                 505                 510

Ile Glu Lys Asp Pro Ala Val Glu Leu Ser Lys Ser Val Ile Ala Ala
            515                 520                 525

Ala Arg Ala Ile Gln Ala Asp Ala Met Ala Asn Ala Tyr Ala Ile Glu
        530                 535                 540

Lys Gly Lys Arg Leu Phe Phe Ala Gly Leu Arg Glu Met Tyr Pro Gly
545                 550                 555                 560

Arg Ala Leu Pro Ser Asp Ala Asn Phe Thr Met Arg Met Ser Tyr Gly
                565                 570                 575

Ser Ile Lys Gly Tyr Glu Pro Gln Asp Gly Ala Trp Tyr Asn Tyr His
                580                 585                 590

Thr Thr Gly Lys Gly Val Leu Glu Lys Gln Asp Pro Lys Ser Asp Glu
            595                 600                 605

Phe Ala Val Gln Glu Asn Ile Leu Asp Leu Phe Arg Thr Lys Asn Tyr
        610                 615                 620

Gly Arg Tyr Ala Glu Asn Gly Gln Leu His Ile Ala Phe Leu Ser Asn
625                 630                 635                 640

Asn Asp Ile Thr Gly Asn Ser Gly Ser Pro Val Phe Asp Lys Asn
                645                 650                 655

Gly Arg Leu Ile Gly Leu Ala Phe Asp Gly Asn Trp Glu Ala Met Ser
            660                 665                 670

Gly Asp Ile Glu Phe Glu Pro Asp Leu Gln Arg Thr Ile Ser Val Asp
        675                 680                 685

Ile Arg Tyr Val Leu Phe Met Ile Asp Lys Trp
690                 695

<210> SEQ ID NO 9
<211> LENGTH: 720
<212> TYPE: PRT
<213> ORGANISM: Porphyromonas gingivalis

<400> SEQUENCE: 9

Met Lys Lys Arg Leu Leu Leu Pro Leu Phe Ala Val Leu Cys Leu Cys
1               5                   10                  15

Gln Ile Ala His Ala Asp Glu Gly Met Trp Leu Met Gln Gln Leu Gly
            20                  25                  30

Arg Lys Tyr Ala Gln Met Lys Glu Arg Gly Leu Lys Met Lys Glu Tyr
        35                  40                  45

Asp Leu Tyr Asn Pro Asn Gly Thr Ser Leu Lys Asp Ala Val Val Leu
    50                  55                  60

Phe Asp Gly Gly Cys Thr Gly Glu Val Val Ser Asp Arg Gly Leu Val
65                  70                  75                  80

Leu Thr Asn His His Cys Gly Tyr Asp Met Ile Gln Ala His Ser Thr
                85                  90                  95

Leu Glu His Asn Tyr Leu Glu Asn Gly Phe Trp Ala Met Arg Glu Ala
```

-continued

```
              100                 105                 110
Asp Glu Leu Pro Asn Lys Asp Ile Ser Val Val Phe Ile Asp Lys Ile
            115                 120                 125
Glu Asp Val Thr Asp Tyr Val Lys Lys Asp Leu Lys Ala Ile Lys Asp
        130                 135                 140
Pro Asn Ser Met Asp Tyr Leu Ser Pro Lys Tyr Leu Gln Lys Leu Ala
145                 150                 155                 160
Asp Lys Lys Ala Gly Lys Asn Phe Ser Ala Lys Asn Pro Gly Leu Ser
                165                 170                 175
Val Glu Ile Lys Ala Phe Tyr Gly Gly Asn Leu Tyr Leu Met Phe Thr
            180                 185                 190
Lys Lys Thr Tyr Thr Asp Val Arg Leu Val Gly Ala Pro Pro Thr Ser
        195                 200                 205
Ile Gly Lys Phe Gly Ala Asp Thr Asp Asn Trp Ile Trp Pro Arg His
210                 215                 220
Thr Gly Asp Phe Ser Ile Phe Arg Ile Tyr Ala Asp Lys Asn Gly Asn
225                 230                 235                 240
Pro Ala Pro Tyr Ser Glu Asp Asn Val Pro Leu Lys Pro Lys Arg Phe
                245                 250                 255
Phe Asn Ile Ser Leu Gly Gly Val Gln Glu Asn Asp Tyr Ala Met Ile
            260                 265                 270
Met Gly Phe Pro Gly Thr Thr His Arg Tyr Phe Thr Ala Ser Glu Val
        275                 280                 285
Asp Glu Trp Lys Ser Ile Asp Asn Asp Ile Arg Ile Arg Met Arg Asp
290                 295                 300
Ile Arg Gln Gly Val Met Leu Arg Glu Met Leu Ala Asp Pro Gln Ile
305                 310                 315                 320
Lys Ile Met Tyr Ser Ala Lys Tyr Ala Ala Ser Gln Asn Ala Tyr Lys
                325                 330                 335
Arg Ala Ile Gly Ala Asn Trp Ala Ile Lys Thr Arg Gly Leu Arg Gln
            340                 345                 350
Asn Lys Gln Ala Met Gln Asp Arg Leu Ile Ala Trp Gly Ala Lys Gln
        355                 360                 365
Gly Thr Pro Arg Tyr Glu Glu Ala Val His Glu Ile Asp Ala Thr Val
        370                 375                 380
Ala Lys Arg Ala Asp Leu Arg Arg Tyr Trp Met Ile Glu Glu Gly
385                 390                 395                 400
Ile Ile Arg Gly Ile Glu Phe Ala Arg Ser Pro Ile Pro Thr Glu Asp
                405                 410                 415
Glu Thr Lys Ala Leu Gln Gly Asn Asp Ala Ser Ala Arg Lys Glu Ala
            420                 425                 430
Ile Asp Lys Ile Arg Thr Arg Tyr Ser Lys Phe Ala Asn Lys Asp Tyr
        435                 440                 445
Ser Ala Glu Val Asp Lys Lys Val Ala Val Ala Met Leu Thr Glu Tyr
    450                 455                 460
Leu Lys Glu Ile Pro Tyr Glu Asn Leu Pro Leu His Leu Arg Leu Val
465                 470                 475                 480
Lys Asp Arg Phe Ala Gly Asp Val Gln Ala Tyr Val Asp Asp Ile Phe
                485                 490                 495
Ala Arg Ser Val Phe Gly Ser Glu Ala Gln Phe Asp Ala Phe Ala Ala
            500                 505                 510
Val Pro Ser Val Glu Lys Leu Ala Glu Asp Pro Met Val Leu Phe Ala
        515                 520                 525
```

-continued

```
Ser Ser Val Phe Asp Glu Tyr Arg Lys Leu Tyr Asn Glu Leu Arg Pro
    530                 535                 540

Tyr Asp Asp Pro Ile Leu Arg Ala Gln Arg Thr Tyr Ile Ala Gly Leu
545                 550                 555                 560

Leu Glu Met Asp Gly Asp Gln Asp Gln Phe Pro Asp Ala Asn Leu Thr
                565                 570                 575

Leu Arg Phe Thr Tyr Gly Gln Val Lys Gly Tyr Ser Pro Arg Asp Asn
            580                 585                 590

Val Tyr Tyr Gly His Gln Thr Thr Leu Asp Gly Val Met Glu Lys Glu
        595                 600                 605

Asp Pro Asp Asn Trp Glu Phe Val Val Asp Pro Lys Leu Lys Ala Val
    610                 615                 620

Tyr Glu Arg Lys Asp Phe Gly Arg Tyr Ala Asp Arg Ser Gly Arg Met
625                 630                 635                 640

Pro Val Ala Phe Cys Ala Thr Thr His Thr Thr Gly Gly Asn Ser Gly
                645                 650                 655

Ser Pro Val Met Asn Ala Asn Gly Glu Leu Ile Gly Leu Asn Phe Asp
            660                 665                 670

Arg Asn Trp Glu Gly Val Gly Gly Asp Ile Gln Tyr Leu Ala Asp Tyr
        675                 680                 685

Gln Arg Ser Ile Ile Val Asp Ile Arg Tyr Val Leu Leu Val Ile Asp
    690                 695                 700

Lys Val Gly Gly Cys Gln Arg Leu Leu Asp Glu Met Asn Ile Val Pro
705                 710                 715                 720
```

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

```
Trp Ala Gly Gly Asp Ala Ser Gly Glu
1               5
```

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

```
Ile Ala Arg Arg His Pro Tyr Phe Leu
1               5
```

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

```
Lys Ile Ala Gly Tyr His Leu Glu Leu
1               5
```

<210> SEQ ID NO 13
<211> LENGTH: 9

```
<212> TYPE: PRT
<213> ORGANISM: Artificial Sequence
<220> FEATURE:
<223> OTHER INFORMATION: Synthetic peptide

<400> SEQUENCE: 13

Phe Leu Arg Glu Pro Val Ile Phe Leu
1               5

<210> SEQ ID NO 14
<211> LENGTH: 13
<212> TYPE: PRT
<213> ORGANISM: Artificial Sequence
<220> FEATURE:
<223> OTHER INFORMATION: Synthetic peptide

<400> SEQUENCE: 14

Trp His Trp Leu Glu Leu Lys Pro Gly Glu Pro Met Tyr
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Synthetic peptide

<400> SEQUENCE: 15

Ser Pro Tyr Ser Ser Glu Thr Thr
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide

<400> SEQUENCE: 16

Ala Pro Val Arg Ser Leu
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide

<400> SEQUENCE: 17

Gln Lys Gln Met Ser Asp Arg Arg Glu
1               5

<210> SEQ ID NO 18
<211> LENGTH: 26
<212> TYPE: PRT
<213> ORGANISM: Porphyromonas gingivalis

<400> SEQUENCE: 18

Ala Asp Lys Gly Met Met Trp Leu Leu Asn Glu Leu Asn Gln Glu Asn
1               5                   10                  15

Leu Asp Arg Met Arg Glu Leu Gly Phe Thr
            20                  25

<210> SEQ ID NO 19
<211> LENGTH: 6
```

```
<212> TYPE: PRT
<213> ORGANISM: Porphyromonas gingivalis

<400> SEQUENCE: 19

Asp Asn Lys Pro Tyr Lys
1               5

<210> SEQ ID NO 20
<211> LENGTH: 5
<212> TYPE: PRT
<213> ORGANISM: Porphyromonas gingivalis

<400> SEQUENCE: 20

Glu Met Thr Tyr Leu
1               5

<210> SEQ ID NO 21
<211> LENGTH: 6
<212> TYPE: PRT
<213> ORGANISM: Porphyromonas gingivalis

<400> SEQUENCE: 21

Phe Ala Gln Phe Ala Asn
1               5

<210> SEQ ID NO 22
<211> LENGTH: 6
<212> TYPE: PRT
<213> ORGANISM: Porphyromonas gingivalis

<400> SEQUENCE: 22

Val Leu Pro Ala Met Leu
1               5

<210> SEQ ID NO 23
<211> LENGTH: 5
<212> TYPE: PRT
<213> ORGANISM: Porphyromonas gingivalis

<400> SEQUENCE: 23

Ser Val Val Pro Tyr
1               5

<210> SEQ ID NO 24
<211> LENGTH: 6
<212> TYPE: PRT
<213> ORGANISM: Porphyromonas gingivalis

<400> SEQUENCE: 24

Leu Phe Phe Ala Gly Leu
1               5

<210> SEQ ID NO 25
<211> LENGTH: 10
<212> TYPE: PRT
<213> ORGANISM: Artificial Sequence
<220> FEATURE:
<223> OTHER INFORMATION: Consensus sequence

<400> SEQUENCE: 25

Thr Gly Gly Asn Ser Gly Ser Pro Val Phe
1               5                   10

<210> SEQ ID NO 26
<211> LENGTH: 9
```

```
<212> TYPE: PRT
<213> ORGANISM: Artificial Sequence
<220> FEATURE:
<223> OTHER INFORMATION: Consensus sequence

<400> SEQUENCE: 26

Thr Gly Gly Asn Ser Gly Ser Pro Val
1               5
```